US012672985B2

(12) United States Patent
Sillerström et al.

(10) Patent No.: US 12,672,985 B2
(45) Date of Patent: Jul. 7, 2026

(54) STRIP ELEMENT FOR AN ABSORBENT HYGIENE ARTICLE

(71) Applicant: Essity Hygiene and Health Aktiebolag, Gothenburg (SE)

(72) Inventors: Filip Sillerström, Mölndal (SE); Rui Pedro Moreira Correia, Gothenburg (SE); Nils Erik Johannes Omberg, Gothenburg (SE); Borja Moises Rojo Perez, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 853 days.

(21) Appl. No.: 18/013,889

(22) PCT Filed: Jun. 30, 2020

(86) PCT No.: PCT/EP2020/068365
§ 371 (c)(1),
(2) Date: Dec. 29, 2022

(87) PCT Pub. No.: WO2022/002364
PCT Pub. Date: Jan. 6, 2022

(65) Prior Publication Data
US 2023/0346608 A1 Nov. 2, 2023

(51) Int. Cl.
*A61F 13/42* (2006.01)
*A61F 13/505* (2006.01)
*G01V 3/08* (2006.01)

(52) U.S. Cl.
CPC ............ *A61F 13/42* (2013.01); *A61F 13/505* (2013.01); *G01V 3/088* (2013.01); *A61F 2013/424* (2013.01)

(58) Field of Classification Search
CPC ... A61F 13/42; A61F 13/505; A61F 2013/424
See application file for complete search history.

(56) References Cited

U.S. PATENT DOCUMENTS

| | | | |
|---|---|---|---|
| 5,281,208 A | 1/1994 | Thompson et al. | |
| 6,593,755 B1 | 7/2003 | Rosengren | |

(Continued)

FOREIGN PATENT DOCUMENTS

| | | |
|---|---|---|
| CN | 101472769 A | 7/2009 |
| CN | 105392456 A | 3/2016 |

(Continued)

OTHER PUBLICATIONS

Chinese Application No. 202080102452.4; Office Action with English translation dated Jun. 30, 2025; 24 pages.

(Continued)

*Primary Examiner* — Catharine L Anderson
(74) *Attorney, Agent, or Firm* — CANTOR COLBURN LLP

(57) ABSTRACT

The present disclosure relates to a strip element configured to be internally or externally, fixedly or removably provided to an absorbent hygiene article, such as a diaper. The strip element comprises at least one sensing element for obtaining excretion-related information in a hygiene article such as a diaper, the sensing element having a capacitor electrode, a signal line, and a ground element such as a ground electrode and/or ground line. The capacitor electrode and the ground element are for measuring an impedance. The capacitor electrode is electrically connected to the signal line. The sensing element further comprises a shielding component provided between the signal line and the ground element. The strip element is configured such that an electric potential of the shielding component synchronously oscillates with an electric potential of the signal line.

20 Claims, 6 Drawing Sheets

(56) References Cited

U.S. PATENT DOCUMENTS

| | | | |
|---|---|---|---|
| 6,828,806 B1 | 12/2004 | Hirota et al. | |
| 7,206,630 B1 | 4/2007 | Tarler | |
| 11,197,785 B2 * | 12/2021 | Mehta | A61F 13/42 |
| 11,280,757 B2 * | 3/2022 | Curran | A61F 13/42 |
| 12,127,921 B2 * | 10/2024 | Lee | A61F 13/44 |
| 2008/0300649 A1 | 12/2008 | Gerber et al. | |
| 2010/0168700 A1 | 7/2010 | Schmidt et al. | |
| 2012/0310190 A1 | 12/2012 | Lavon et al. | |
| 2013/0018340 A1 | 1/2013 | Abraham et al. | |
| 2013/0131618 A1 | 5/2013 | Abraham et al. | |
| 2013/0303867 A1 | 11/2013 | Elfstrom et al. | |
| 2015/0042489 A1 | 2/2015 | Lavon | |
| 2016/0095527 A1 | 4/2016 | Thng et al. | |
| 2018/0104114 A1 | 4/2018 | Pepin et al. | |
| 2018/0333306 A1 | 11/2018 | Ahong et al. | |
| 2019/0154607 A1 | 5/2019 | Tuli | |
| 2019/0240079 A1 | 8/2019 | Tuli | |
| 2019/0247241 A1 | 8/2019 | Porthiyas et al. | |
| 2019/0290501 A1 | 9/2019 | Lavon et al. | |
| 2020/0196933 A1 | 6/2020 | Van Keymeulen et al. | |
| 2021/0187189 A1 | 6/2021 | Yuds et al. | |
| 2021/0393448 A1 | 12/2021 | Wang et al. | |
| 2022/0054326 A1 * | 2/2022 | Öberg | A61B 5/053 |
| 2023/0277391 A1 | 9/2023 | Sillerström et al. | |
| 2023/0284977 A1 | 9/2023 | Sillerström et al. | |
| 2023/0346608 A1 | 11/2023 | Sillerström et al. | |
| 2024/0382350 A1 | 11/2024 | Sillerström et al. | |

FOREIGN PATENT DOCUMENTS

| | | | |
|---|---|---|---|
| CN | 107530214 A | 1/2018 | |
| CN | 107765931 A | 3/2018 | |
| EP | 2272472 A1 | 1/2011 | |
| EP | 2713973 A1 | 4/2014 | |
| EP | 3449814 A1 | 3/2019 | |
| FR | 1476299 A | 4/1967 | |
| GB | 466124 A | 5/1937 | |
| GB | 486017 A | 5/1938 | |
| JP | 2003075480 A | 3/2003 | |
| JP | 2006012159 A | 1/2006 | |
| WO | 9614813 A1 | 5/1996 | |
| WO | 2015102085 A1 | 7/2015 | |
| WO | 2016090492 A1 | 6/2016 | |
| WO | 2019096413 A1 | 5/2019 | |
| WO | 2020126000 A1 | 6/2020 | |
| WO | 2021033911 A2 | 2/2021 | |
| WO | 2022002361 A1 | 1/2022 | |
| WO | 2022002362 A1 | 1/2022 | |
| WO | 2022002363 A1 | 1/2022 | |

OTHER PUBLICATIONS

Chinese Application No. 202080102452.4; Office Action dated Dec. 31, 2024; 20 pages.

Chinese Application No. 202080102646.4; Office Action dated Dec. 19, 2024; 14 pages.

U.S. Appl. No. 18/013,887; Non Final Office Action dated May 27, 2025; 25 pages.

U.S. Appl. No. 18/013,892; Non Final Office Action dated May 7, 2025; 26 pages.

International Search Report & Written Opinion for International Application No. PCT/EP2020/068361; International Filing Date: Jun. 30, 2020; Date of Mailing: Apr. 7, 2021; 9 pages.

International Search Report & Written Opinion for International Application No. PCT/EP2020/068362; International Filing Date: Jun. 30, 2020; Date of Mailing: Apr. 7, 2021; 14 pages.

International Search Report & Written Opinion for International Application No. PCT/EP2020/068363; International Filing Date: Jun. 30, 2020; Date of Mailing: Apr. 7, 2021; 11 pages.

International Search Report & Written Opinion for International Application No. PCT/EP2020/068365; International Filing Date: Jun. 30, 2020; Date of Mailing: Apr. 12, 2021; 12 pages.

US Non-Final Office Action, U.S. Appl. No. 18/013,844, mailed Jan. 22, 2026; 29 pages.

Australian Office Action, Application No. 2020456199, mailed Mar. 17, 2026, 5 pages.

* cited by examiner

40

44

44

44

44

44

102

45

45

45

45

45

58

$T_{PCB}$

52

54

50

48

42

42

42

48

$W_{PCB}$

56

42

48

$L_{PCB}$

60

104

105

103

$T_S$

40

44

44

44

44

104

105

103

44

$W_S$ $L_S$

STRIP ELEMENT FOR AN ABSORBENT HYGIENE ARTICLE

CROSS REFERENCE TO RELATED APPLICATIONS

This application is a National Stage application of PCT/EP2020/068365, filed Jun. 30, 2020, which is incorporated by reference in its entirety herein.

TECHNICAL FIELD

The present disclosure relates to a strip element configured to be internally or externally, fixedly or removably provided to an absorbent hygiene article, such as a diaper. The present disclosure further relates to a use of the strip element, and to a hygiene system comprising the strip element and the absorbent hygiene article.

BACKGROUND ART

Systems for monitoring incontinence are known in the art. For instance, WO 96/14813 A1 discloses an incontinence monitoring system for persons wearing an absorbent hygiene article, and is particularly concerned with a system for detection, monitoring and management of urinary, fecal and other forms of incontinence in the absorbent hygiene article. The system comprises a plurality of sensors and a monitor to receive and record signals from the sensors, each sensor being adapted to be associated with a respective person and being responsive to urinary and/or fecal incontinence in that person.

A disadvantage of the system disclosed in WO 96/14813 A1 however, resides in that the utilized sensing technology is not particularly accurate. That is, in some cases, a single drop of urine may suffice to trigger the sensor to signal the presence of an incontinence event. Likewise, the sensor may in some cases be triggered by other types of liquid such as transpiration or menstrual blood. Besides the latter "false positive" signals, there may also be an increased risk of "false negative" events. For example, if an amount of urine were to be absorbed by a specific portion of an absorbent article not comprising the sensor, no signal would be triggered despite the presence of an incontinence event.

Another disadvantage of the system of WO 96/14813 A1 resides in that an actual amount of excretion or a saturation of an absorbent hygiene article may not be precisely determined. It may, e.g., be the case that the system signals that an absorbent article is to be replaced even if the absorbent article has absorbed only a small amount of urine. Such cases would have to be associated with disadvantages as regards an environmental impact as well as sustainable use of raw materials.

Yet another disadvantage of the system of WO 96/14813 A1 resides in the position of the sensor in relation to the absorbent article. That is, as the sensor needs to be accommodated by a cavity in an absorbing material, a special tool is necessary to apply the sensor to the absorbent article. Moreover, it appears that the system only works with special, customized absorbent articles tailored to the shape of the sensor. On top of that, as the set position of the sensor is a position relatively close to the skin of a wearer, inconveniences such as pressure marks or skin irritations may be caused by the sensor.

Moreover, the concept of WO 96/14813 A1 relies upon direct (i.e., galvanic) contact between the sensor and the excretion to be detected. Hence, at least for hygienic reasons, the sensor needs to be replaced and/or cleaned periodically. Such cleaning and/or replacing may go along with disadvantages as regards environmental sustainability as well as operating costs of the system.

Even though the system of WO 96/14813 A1 is intended for use in hospitals or nursing homes, the problem of monitoring incontinence is not limited to such applications. In fact, monitoring of incontinence may also be of interest, e.g., for newborns or infants accommodated in day care centers or in private homes. However, especially in the latter cases, low operating costs appear to be of major importance for establishing such systems in large scales.

SUMMARY

It is an objective of the present disclosure to overcome at least one of the above-mentioned disadvantages in a simple but nevertheless effective way.

A strip element in accordance with the present disclosure is defined in claim 1. A use of a strip element is defined in claim 14. Another strip element in accordance with the present disclosure is defined in claim 15. A hygiene system in accordance with the present disclosure is defined in claim 18. Dependent claims relate to preferred embodiments.

A strip element in accordance with the present disclosure is a strip element configured to be internally or externally, fixedly or removably provided to an absorbent hygiene article, such as a diaper. The strip element comprises at least a first sensing element for measuring an impedance, the first sensing element having a capacitor electrode, a signal line, and a ground element. The ground element may be a ground electrode and/or ground line. The capacitor electrode is electrically connected to the signal line. The first sensing element further comprises a shielding component provided between the signal line and the ground element. The strip element is configured such that an electric potential of the shielding component synchronously oscillates with an electric potential of the signal line.

The strip element may be configured to be repeatedly attachable to and detachable from a garment facing surface of the absorbent hygiene article.

If the strip element is attached to a garment facing surface of an absorbent hygiene article which has absorbed liquid, the first sensing element may measure another value of impedance than in a case in which the absorbent hygiene article has not absorbed liquid. In other words, a value of impedance measured by the first sensing element may vary (e.g., decrease) in response to the introduction of liquid, such as urine, into the absorbent hygiene article. The strip element may, hence, be used for detecting the presence of a liquid, such as urine, in (a portion of) the absorbent hygiene article. However, as the first sensing element of the strip element is a sensing element for measuring an impedance, no galvanic contact between the strip element (or components thereof) and the liquid is needed for detecting the presence of liquid. Consequently, the strip element does not need to be cleaned or replaced on a regular basis.

The concept of detecting a liquid by virtue of a sensing element for measuring an impedance allows obtaining a configuration in which the strip element is attachable to a garment facing surface of an absorbent hygiene article. The latter location may, in turn, be associated with reduced effort as regards an application and/or removal of the strip element. In particular, no special tool needs to be utilized in order to attach or remove the strip element. Moreover, the attaching and/or detaching may take place even while a person such as an infant or a patient wears the absorbent hygiene article.

As an electric potential of the shielding component synchronously oscillates with an electric potential of the signal line, the shielding component may be considered an "active shield". Utilizing such a shielding component may be associated with the technical effect of increasing a measurement accuracy of the first sensing element and/or making the first sensing element less susceptible for external influences such as electromagnetic interferences. The provision of the shielding component may, e.g., aid in distinguishing between an impedance to be measured by the first sensing element, and interfering signals caused by other electrically operated elements which may be located nearby. Distinguishing between an impedance to be measured and interfering signals may, in particular, be promoted if an interfering signal is an oscillating signal.

In the present context, the concept of "synchronous oscillation" includes: cases in which an electric potential of the signal line and an electric potential of the shielding component are continuously the same potential (i.e., the oscillation curves are substantially identical); and cases in which an electric potential of the signal line and an electric potential of the shielding component oscillate in the same frequency and without any phase shift (i.e., without any time related phase shift). In the latter case, an oscillation amplitude of the potential of the signal line, and an oscillation amplitude of the potential of the shielding component may be different amplitudes (also comprising amplitudes having opposite amplitude directions).

Alternatively or additionally, the concept of "synchronous oscillation" includes a case in which an oscillation curve of an electric potential of the shielding component and an oscillation curve of an electric potential of the signal line share the points of their respective zero-crossings (i.e., points of intersecting a time-axis).

An electric potential of the signal line (and, hence, also of the shielding component) may oscillate, e.g., between 0 V and a first positive value such as 5, 4, 3 or 2 V, when compared to a grounded potential. Alternatively, an electric potential of the signal line (and, hence, also of the shielding component) may oscillate, e.g., between a first negative value such as −5, −4-, −3 or −2 V and a and a second positive value such as 5, 4, 3 or 2 V, when compared to a grounded potential. An oscillation frequency of the potential of the signal line (and, hence, also of the potential of the shielding component) may, e.g., be from 10, 20, 30 or 40 kHz to 100, 90, 80, 70 or 60 kHz. Optionally, an oscillation frequency of the potential of the signal line (and, hence, also of the potential of the shielding component) is a constant oscillation frequency.

According to some aspects, the strip element further comprises a second sensing element for measuring an impedance. The second sensing element has a second capacitor electrode, a second signal line, and a second ground element. The second ground element may be a second ground electrode and/or a second ground line. The second capacitor electrode is electrically connected to the second signal line. The second sensing element further comprises a second shielding component provided between the second signal line and the second ground element. The strip element is configured such that an electric potential of the second shielding component synchronously oscillates with an electric potential of the second signal line. Optionally, the first shielding component and the second shielding component are the same shielding component, or different shielding components. The first shielding component and the second shielding component may be electrically connected to each other, or electrically insulated from each other.

A strip element comprising a second sensing element as described above may be associated with the technical effect of promoting increased measurement accuracy. That is, if a second sensing element is provided in addition to the first sensing element, measurement of an impedance may be enabled in at least two portions of the absorbent hygiene article. It may, hence, be possible to determine the presence of a liquid in the absorbent hygiene article even if the liquid has not been introduced into a portion associated with a location of the first sensing element. Therefore, it may be less likely to receive a "false negative" measurement result.

Moreover, the presence of more than one sensing element (e.g., a first sensing element and a second sensing element) may allow drawing conclusions as regards a saturation of the absorbent hygiene article. For example, if the first sensing element measures an impedance indicating that liquid is present in a portion associated with the sensing element, and the second sensing element measures an impedance indicating that no liquid is present in a portion associated with the second sensing element, it might not yet be necessary to replace the absorbent hygiene article. Due to the ability to counteract against unnecessary replacement of the absorbent hygiene article, the strip element comprising a second sensing element may be associated with reduced operational cost as well as positive impact on environmental sustainability.

As an electric potential of the second shielding component synchronously oscillates with an electric potential of the signal line, the second shielding component may also be considered an "active shield". Utilizing such a second shielding component may be associated with the technical effect of increasing a measurement accuracy of the second sensing element and/or making the second sensing element less susceptible for external influences such as electromagnetic interferences. The provision of the second shielding component may, e.g., aid in distinguishing between an impedance to be measured by the second sensing element, and interfering signals caused by other electrically operated elements. Distinguishing between an impedance to be measured and interfering signals may, in particular, be promoted if an interfering signal is an oscillating signal. If a first sensing element and a second sensing element are provided, mutual interferences between signals of the first sensing element and signals of the second sensing element may occur. The risk of the first sensing element or the second sensing element corrupting a measurement result of the respectively other sensing element may, however, be reduced due to the provision of the shielding component and the second shielding component.

According to some aspects, an oscillation frequency of the potential of the signal line and an oscillation frequency of the potential of the second signal line are different oscillation frequencies. Alternatively or additionally, an oscillation frequency of the potential of the signal line and an oscillation frequency of the potential of the second signal line may be phase-shifted with respect to each other. In the latter case, the oscillation frequency of the potential of the signal line and an oscillation frequency of the potential of the second signal line may be the same oscillation frequency.

Utilizing different oscillation frequencies and/or phase-shifted frequencies may aid in distinguishing between an impedance measured by the first sensing element and an impedance measured by the second sensing element.

According to some aspects, the strip element further comprises a third sensing element for measuring an impedance. The third sensing element has a third capacitor electrode, a third signal line, and a third ground element. The third ground element may be a third ground electrode and/or a third ground line. The third capacitor electrode is electrically connected to the third signal line. The third sensing element further comprises a third shielding component provided between the third signal line and the third ground element. The strip element is configured such that an electric potential of the third shielding component synchronously oscillates with an electric potential of the third signal line. The first shielding component, the second shielding component, and the third shielding component may be the same shielding component or different shielding components. The first shielding component, the second shielding component, and the third shielding component may be electrically connected to each other, or electrically isolated from each other.

According to some aspects, an oscillation frequency of the potential of the signal line, an oscillation frequency of the potential of the second signal line and an oscillation frequency of the potential of the third signal line are different oscillation frequencies. Alternatively or additionally, an oscillation frequency of the potential of the signal line, an oscillation frequency of the potential of the second signal line, and an oscillation frequency of the potential of the third signal line may be phase-shifted with respect to each other. In the latter case, the oscillation frequency of the potential of the signal line, an oscillation frequency of the potential of the second signal line, and an oscillation frequency of the potential of the third signal line may be the same oscillation frequency.

According to some aspects, the strip element further comprises a fourth sensing element for measuring an impedance. The fourth sensing element has a fourth capacitor electrode, a fourth signal line, and a fourth ground element. The fourth ground element may be a fourth ground electrode and/or a fourth ground line. The fourth capacitor electrode is electrically connected to the fourth signal line. The fourth sensing element further comprises a fourth shielding component provided between the fourth signal line and the fourth ground element. The strip element is configured such that an electric potential of the fourth shielding component synchronously oscillates with an electric potential of the fourth signal line. The first shielding component, the second shielding component, the third shielding component and the fourth shielding component may be the same shielding component and/or a different shielding component. The first shielding component, the second shielding component, the third shielding component and the fourth shielding component may be electrically connected to each other, or electrically insulated from each other.

According to some aspects, an oscillation frequency of the potential of the signal line, an oscillation frequency of the potential of the second signal line, an oscillation frequency of the potential of the third signal line, and an oscillation frequency of the potential of the fourth signal line are different oscillation frequencies. Alternatively or additionally, an oscillation frequency of the potential of the signal line, an oscillation frequency of the potential of the second signal line, an oscillation frequency of the potential of the third signal line, and an oscillation frequency of the potential of the fourth signal line may be phase-shifted with respect to each other. In the latter case, the oscillation frequency of the potential of the signal line, an oscillation frequency of the potential of the second signal line, an oscillation frequency of the potential of the third signal line, and an oscillation frequency of the potential of the fourth signal line may be the same oscillation frequency.

A configuration in which respective shielding components are electrically connected to each other may be associated with a cost-efficient layout while still promoting ease of distinction between signals associated with different sensing elements.

It is to be understood that the above-described advantages and technical effects associated with more than one sensing elements may apply even more if three sensing elements, four sensing elements, or more than four sensing elements are provided.

According to some aspects, the strip element comprises a first processing module configured to provide the respective signal line and/or the respective shielding component of the first sensing element, the second sensing element, the third sensing element and/or the fourth sensing element with oscillating potentials.

According to some aspects, the strip element comprises a second processing module configured to obtain an impedance of the first sensing element, the second sensing element, the third sensing element and/or the fourth sensing element, respectively.

The first processing module and the second processing module may be the same processing module or different processing modules.

According to some aspects, the ground element comprises a ground electrode and a ground line electrically connected thereto, wherein the shielding component is provided between the signal line and the ground electrode, and also between the signal line and the ground line. If more than one sensing element is provided, this configuration may be adopted by the respectively other sensing elements.

The above-described configuration may be associated with optimized shielding performance. Specifically, the above-described configuration may aid in preventing interference signals having an impact on the ground line as well as interference signals having an impact on the ground electrode.

According to some aspects, the shielding component is, at least partially, provided between the capacitor electrode and the signal line. If more than one sensing element is provided, this configuration may be adopted by the respectively other sensing elements.

A shielding component which is, at least partially, provided between the capacitor electrode and the signal line may be considered an efficient way of providing the shielding component such that it can reliably fulfil the task of preventing external interferences.

According to some aspects, the shielding component comprises an opening in which a portion of the signal line is provided so as to be guided from a first side of the shielding component to a second side of the shielding component, the first side being a side in which the capacitor electrode is provided. If more than one sensing element is provided, this configuration may be adopted by the respectively other sensing elements.

The above-described configuration may allow cost-efficient production of a slim strip element in which a plurality of components for promoting measurement accuracy are provided.

According to some aspects, the strip element comprises a plurality of layers including first to third layers stacked in numerical order. The first layer includes at least one of, optionally both of the ground electrode and the capacitor electrode. The second layer includes the shielding component. The third layer includes at least parts of the signal line.

If more than one sensing element is provided, this configuration may be adopted by the respectively other sensing elements. That is, in the latter case, each of the ground electrode, the second ground electrode, the third ground electrode and/or the fourth ground electrode may be included in the first layer. Moreover, each of the capacitor electrode, the second capacitor electrode, the third capacitor electrode and the fourth capacitor electrode may be included in the first layer. Moreover, each of the shielding component, the second shielding component, the third shielding component and/or the fourth shielding component may be included in the second layer. Moreover, at least parts of the signal line, the second signal line, the third signal line and/or the fourth signal line may be included in the third layer.

Optionally, the first to third layers are substantially parallel. It is to be noted that, in the present context, the term "parallel" does not necessarily imply that the layers need to have a planar extension. Even though the layers may be planar, the term "parallel" merely relates to a state in which respectively adjacent layers have a substantially constant distance to each other. This state may explicitly include layers having a curved shape, or flexible layers configured to be bent with respect to one or several axes.

According to some aspects, an insulating layer is provided between the first layer and the second layer, and between the second layer and the third layer.

The above-described configuration utilizing layers may facilitate cost-efficient manufacturing of at least components of the strip element.

According to some aspects, the first to third layers are layers of a flexible printed circuit board. In this context it is to be understood that, even though rather rigid or stiff materials and/or devices may be associated with a particular amount of flexibility, a person skilled in the art is capable of determining whether a printed circuit board is a flexible printed circuit board or not.

Utilizing a flexible printed circuit board may be considered a cost-efficient and effective way of providing a strip element configured to be internally or externally, fixedly or removably provided to an absorbent hygiene article, such as a diaper. Moreover, since a garment facing surface of a hygiene articles such as a diaper may be flexible as well, promoting flexibility of the strip element by using a flexible printed circuit board may further promote wearing comfort of an absorbent hygiene article to which the strip element is attached.

According to some aspects, the flexible printed circuit board comprises at least one of: polyimide; polyester; polytetrafluoroethylene; aramid; and polyethylene naphthalate.

The above-mentioned materials may be associated with mechanical and/or electrical properties contributing to having an optimized amount of flexibility while ensuring compliance with electrical safety requirements.

According to some aspects, the flexible printed circuit board comprises the first sensing element, the second sensing element, the third sensing element and/or the fourth sensing element.

A strip element in which some of, or all of the sensing elements are included in the flexible printed circuit board may be associated with cost-efficient production while promoting a high amount of flexibility of the strip element. This may, in turn, mutually contribute to the above-discussed technical effects regarding wearing comfort. Moreover, such a configuration may contribute to promoting close contact between the strip element and the absorbent hygiene article, even if a person wearing the absorbent hygiene article moves.

According to some aspects, the shielding component is continuously provided between the ground element and the signal line such that there is no portion of the respective sensing element in which the shielding component is not provided between the ground element and the signal line. Optionally, the ground element includes a ground electrode and a ground line. If more than one sensing element is provided, this configuration may be adopted by the respectively other sensing elements.

A configuration in which the shielding component is continuously provided as described above may be associated with promoting shielding performance. That is, in the above-described configuration, external interferences may be prevented in many portions of the sensing element, thus, further reducing an error susceptibility of the sensing element.

According to some aspects, the ground element comprises a ground electrode and a ground line electrically connected thereto, wherein the shielding component is continuously provided between the ground electrode and the signal line such that there is no portion of the sensing element in which the shielding component is not provided between the ground electrode and the signal line. Optionally, the shielding component is not provided between the ground line and the signal line.

The latter configuration may be considered advantageous, e.g., in cases where potential external interferences mainly occur in portions corresponding to the ground electrode. In such cases, the above-described configuration may be considered a compromise between promoting low manufacturing costs of the strip element (e.g., due to an absence of the shielding component between the signal line and the ground line), and taking measures against external interferences potentially distorting signals of the sensing element(s).

A use in accordance with the present disclosure is a use of any one of the above-described strip elements, wherein the first layer is provided closer to a garment facing surface of an absorbent hygiene article, such as a diaper, than the second layer and/or the third layer.

The above-described use may be associated with a configuration in which the presence of liquid in the absorbent hygiene article will most likely lead to a variation in the impedance measured by the first sensing element, the second sensing element, the third sensing element and/or the fourth sensing element. The variation in the impedance measured by the respective sensing element may, in particular, be more distinct in the above-described use than in other uses such as a use in which the first layer is provided more distant to the garment facing surface of the absorbent hygiene article than the first and/or second layer. The above-described use may, hence, be associated with an increased measurement accuracy and/or measuring performance.

A second strip element in accordance with the present disclosure is a strip element configured to be internally or externally, fixedly or removably provided to an absorbent hygiene article, such as a diaper. Optionally, this strip element is any one of the previously described strip elements. The second strip element comprises a sensing element having a capacitor electrode, a signal line, and a ground element such as a ground electrode and/or ground line. The capacitor electrode is electrically connected to the signal line. One of the capacitor electrode and the ground element is provided so as to form an open or a closed loop around the other one of the capacitor electrode and the ground element. The sensing element of the second strip element may correspond to the first sensing element of any one of the previously described strip elements. If the second strip element comprises more than one sensing element, configurations of the above-described second sensing elements, third sensing elements, and/or fourth sensing elements may be adopted so as to correspond to the configuration of the sensing element of the second strip element.

The second strip element may be configured to be repeatedly attachable to and detachable from a garment facing surface of the absorbent hygiene article.

A first element forming an open or closed loop around a second element may alternatively be described as a configuration in which the first element partially or fully surrounds the second element. The surrounding may comprise two-dimensional surrounding (which does not necessarily mean planar surrounding), or three-dimensional surrounding such as spherical or cubic surrounding. The first element forming an open or closed loop around the second element may, e.g., at least partially have the shape of a circle, a segment of a circle, a rectangle or the like. The degree of surrounding may, e.g., be at least 180°, at least 270°, or at least 340°.

A configuration in which one of the capacitor electrode and the ground element forms an open or closed loop around the other one of the capacitor electrode and the ground element may promote measurement accuracy of the sensing element. A reason is that a variation of a distance between the capacitor electrode and the ground element may affect a value of impedance to be measured by the sensing element. In configurations deviating from the above-described open or closed loop, bending of the sensing element may result in falsified measurement results. In the open or closed loop configuration, however, a reduction of a distance between the capacitor electrode and the ground element in a first portion of the sensing element may go along with an increased distance in another portion of the sensing element. The configuration involving the open or closed loop may, hence, be considered to compensate external influences on the measured impedance.

According to some aspects, a ground electrode of the ground element is formed so as to form an open or closed loop around the capacitor electrode.

The latter aspects may be associated with a configuration in which the capacitor electrode is provided in a central portion of the sensing element. Such configurations may, in turn, allow precise measurements due to a clearly delimited measuring region.

According to some aspects, a ground electrode of the ground element is provided in a first layer of a flexible printed circuit board, and the capacitor electrode is provided in a layer of the flexible printed circuit board. Optionally, the first layer comprising the ground electrode and the layer comprising the capacitor electrode are the same layers.

As regards advantages and/or technical effects of utilizing a flexible printed circuit board, reference is made to earlier passages discussing such features. It is to be understood that these advantages and/or technical effects apply to the latter aspects analogously. Moreover, the configuration in which the first layer comprising the ground electrode and the layer comprising the capacitor electrode are the same layers may be particularly advantageous as regards promoting production efficiency of the sensing element. The reason is that, in this configuration, only one layer is necessary for both elements. Moreover, the latter configuration allows providing a thinner sensing element, which may promote wearing comfort of an absorbent hygiene article to which the strip element is attached.

A third strip element in accordance with the present disclosure is a strip element configured to be externally and removably provided to an absorbent hygiene article, such as a diaper. The third strip element comprises at least two sensing elements for obtaining excretion-related information in an absorbent hygiene article, such as a diaper. The third strip element further comprises at least two close contact sensing zones for being removably attached to a garment facing surface of the absorbent hygiene article, respectively. Each of the at least two close contact sensing zones comprises one of the at least two sensing elements. Each close contact sensing zone comprises first attachment means for keeping the close contact sensing zone in contact with the absorbent hygiene article by a first attachment force. The two close contact sensing zones are separated by a flex zone which is either free of any attachment means or comprises second attachment means for establishing a second attachment force between the flex zone and the absorbent hygiene article, the second attachment force being a smaller force than the first contact force.

The third strip element may be configured to be repeatedly attachable to and detachable from a garment facing surface of the absorbent hygiene article.

Optionally, the third strip element is any one of the previously described first and/or second strip elements.

Attachment forces such as the first attachment force and the second attachment force may be determined, e.g., according to a modified version of ASTM D5170—Standard Test Method for Peel Strength ("T" Method) of Hook and Loop Touch Fasteners. The testing may be made in a stable environment set, e.g., to 23° C. and, e.g., 50% relative humidity.

As regards the test equipment, a tensile tester (such as available from Lloyd Instruments, Instron or MTS Systems), equipped with two clamps at least 50 mm wide may be utilized. The tensile tester may be connected to a computer with software able to chart stress versus separation distance. Moreover, a cylindrical roller having a smooth steel surface may be provided. The roller may be, e.g., 57 mm wide, may have a diameter of, e.g., 121 mm and may weigh, e.g., 5 kg. Optionally, the roller may be inserted into an apparatus able to move it forward, e.g., at a rate of about 500 mm/min. Alternatively, a manual arrangement may be provided. Moreover, a polyester textile cloth (e.g., 75 gsm), available, e.g., from Paul Uebel Wirk-und Strickwaren GmbH, article number 27 18 (or equivalent) may be provided. A test substrate may be cut or punched to a width of, e.g., 50 mm, and to a length coinciding with the length of the strip element. The length direction of the test substrate should coincide with the cross direction (CD) of the cloth (as taken from the supplier's roll). Moreover, low elongation tape, quality 4591 (glass fibre reinforced) from Tesa, 50 mm wide may be utilized in the test.

As regards the test procedure, the cloth substrate may be prepared by first placing it flat on a smooth steel surface. The low elongation tape may then be aligned on top. The roller may then be pushed over the tape for one cycle (back and forth) at rate of about 500 mm/min. The tape should extend about, e.g., 5 cm from one end of the cloth (folded over itself to eliminate stickiness), to create a grip area when inserting the sample into the clamps of the tensile tester. A grip area is likewise prepared for the strip element by attaching tape, e.g., 5 cm into one end of the strip, with a grip area extending for, e.g., about 5 cm. The length of the strip element may be placed flat and centered along the length of the prepared cloth, with a smooth steel surface underneath. The roller may then be pushed along the length of the strip element for one cycle (back and forth) at a rate of, e.g., 500 mm/min. On the tensile tester, the clamps may be positioned, e.g., 25 mm apart, and the upper clamp (which may be a movable clamp) may be set to raise at a speed of, e.g., 300 mm/min. The grip areas may then be inserted into the clamps, with the grip area of the strip element in the upper (movable) clamp. The test may then be started, and the sensor element and the cloth may be completely separated (i.e. over the whole sample length). During the test, the (yet unseparated) end of the sensor element may be gently and carefully held, e.g., at an about 90 degrees angle versus the vertical plane between the clamps, so that the weight of the sensor strip does not unduly influence the result. On a graph representing stress versus separation distance, the attachment forces over the close contact sensing zones and the flex zones may be registered. The forces are then related to the width of the attachment means, so that results in the unit Newtons per cm of width can be calculated. The arithmetic mean values (in N/cm) may then be compared for the sensing zone (first attachment force) and flex zone (second attachment force).

The above-described configuration may be associated with the technical effect of preventing measurement errors. A reason may lie in that the flex zones may act as "intended detaching zones" if an external force is applied to the strip element. Generally, if an external force is applied to the strip element (e.g., due to movement of a person wearing an absorbent hygiene article to which the strip element is attached), the risk exists that portions of the strip element detach from a garment facing surface of the absorbent hygiene article. If the detaching portion of the strip element were to be a portion comprising a sensing element, a sensing result could be falsified. However, in view of the first attachment force being smaller than the second attachment force, it may be likely that the flex zone detaches from the garment facing surface of the absorbent hygiene article in response to an external force, while the close contact sensing zones remain in contact with the garment facing surface of the absorbent hygiene article.

An advantage of the strip element being configured to be removable may reside in a reusability of the strip element. In this regard, it is to be noted that the reusability of the strip element may be promoted despite a disposable nature of the absorbent product. An advantage of the strip element being configured to be externally provided to the absorbent hygiene article may lie in that there is no need to integrate electronic/metallic components into the absorbent product. Moreover, the removability and the external provision may synergistically contribute to promoting ease of cleaning of the strip element.

Moreover, the above-described configuration may be associated with the technical effect of promoting comfort of a user wearing an absorbent hygiene article to which the strip element is attached. A reason may lie in that the flex zone may absorb an external force applied to the strip element by detaching from the garment facing surface of the absorbent hygiene article. Due to the detaching, the flex zone may interrupt a flow of forces that would otherwise have been transferred to a wearer, thereby eventually causing pressure marks or other kinds of irritations.

According to some aspects, no sensor is provided in the flex zone.

If no sensor is provided in the flex zone, the above-described effects regarding measurement accuracy may be further promoted. That is, in such configurations, not only would the sensing elements of the close contact sensing zones most likely remain in contact with the garment facing surface of the absorbent hygiene article, but also would no sensor detach from the garment facing surface of the absorbent hygiene article if the flex zone were to detach as described above.

According to some aspects, the first attachment means comprises mechanical attachment means such as attachment means utilizing hook-fasteners, or adhesive-based attachment means. Alternatively or additionally, the second attachment means may comprise mechanical attachment means such as an attachment means utilizing hook-fasteners, or adhesive-based attachment means.

If hook-fasteners (i.e., hook-and-loop fasteners such as Velcro) are utilized, one of a hooks-comprising element and a loop-comprising element may be included in the strip element, while the other one of the hooks-comprising element and the loop-comprising element may be provided on a garment facing surface of a diaper. It is, hence, to be understood that, in the present context, the concept of comprising "hook-fasteners" may involve a case in which the strip element comprises only one element of a hook-and-loop fastening system. This one element does not necessarily need to be the hook-comprising element but may also be a loop-comprising element.

According to some aspects, the mechanical attachment means is configured such that attachment is possible even if no counterpart is provided on the garment facing surface of the absorbent hygiene article. An example of such attachment means may involve hook-fasteners having a configuration to engage with materials commonly used for garment facing surfaces of absorbent hygiene articles.

Utilizing mechanical attachment means as described above may be advantageous as such attachment means may be repeatedly attached and detached without significant loss of attachment force. Moreover, mechanical attachment means may provide a cost-efficient way of attaching the strip element to a garment facing surface of an absorbent hygiene article.

Utilizing adhesive based attachment means as described above may be advantageous as such attachment means are available in very low thicknesses. Adhesive-based attachment means may, hence, be associated with low space consumption. Moreover, such attachment means may have very high mechanical flexibility. The low space consumption and the high degree of mechanical flexibility may mutually contribute to further promoting wearing comfort of an absorbent hygiene article to which the strip element is attached.

A fourth strip element in accordance with the present disclosure is a strip element configured to be internally or externally, fixedly or removably provided to an absorbent hygiene article, such as a diaper. The fourth strip element comprises at least two sensing elements for obtaining excretion-related information in an absorbent hygiene article, such as a diaper. The strip element further comprises at least two sensing zones, each of which comprises one of the at least two sensing elements. The two sensing zones are separated by a deformation susceptibility zone that connects the two sensing zones and that is free of any sensing element. The deformation susceptibility zone has lower bending stiffness than the respectively adjacent sensing zones.

The fourth strip element may be configured to be repeatedly attachable to and detachable from a garment facing surface of the absorbent hygiene article.

Optionally, the fourth strip element is any one of the previously described first, second and/or third strip elements. The sensing zones may, e.g., be or comprise the close contact sensing zones. The deformation susceptibility zone may, e.g., be or comprise the flex zone.

A bending stiffness such as a bending stiffness of the deformation susceptibility zone or a bending stiffness of the sensing zones may be determined in accordance with the well-known three-point bending principle (as found e.g. in ISO 178 or ASTM D790). The zones under investigation may, e.g., be cut out from the strip element. In case the zones have different lengths, the longer zone may be cut to the same length as the shorter. The zone under investigation may then be placed flat over a support span (e.g., a support span having two beams), with the longitudinal ends of the zone (as viewed on the uncut strip) resting on the beams. The side having the attachment means may face upwards. A probe may then push from above onto a central point of the strip zone to be measured. As the probe pushes downwards, the respective zone may deflect and either brake or reach a point where it falls through the support span. Either way, a maximum force measured during the testing may be read, and the value may be compared to other zones tested according to the identical procedure. The test can easily be adopted to different strip element configurations, e.g. by altering the distance of the support span, or by using a small probe if only short zones can be extracted.

The above-described configuration may be associated with the technical effect of preventing measurement errors. A reason may lie in that the deformation susceptibility zones may act as "intended detaching zones" if an external force is applied to the strip element. Generally, if an external force is applied to the strip element (e.g., due to movement of a person wearing an absorbent hygiene article to which the strip element is attached), the risk exists that portions of the strip element detach from a garment facing surface of the absorbent hygiene article. If the detaching portion of the strip element were to be a portion comprising a sensing element, a sensing result could be falsified. However, in view of a bending stiffness of the deformation susceptibility zone being smaller than a bending stiffness of sensing zones, it may be likely that the deformation susceptibility zone detaches from the garment facing surface of the absorbent hygiene article in response to an external force, while the sensing zones remain in contact with the garment facing surface of the absorbent hygiene article.

Moreover, the above-described configuration may be associated with the technical effect of promoting comfort of a user wearing an absorbent hygiene article to which the strip element is attached. A reason may lie in that the deformation susceptibility zone may absorb an external force applied to the strip element by being bent before a sensing zone is bent. Due to the bending, the deformation susceptibility zone may interrupt a flow of forces that would otherwise have been transferred to a wearer, thereby eventually causing pressure marks or other kinds of irritations.

If the deformation susceptibility zone is included in, comprises, or is the flex zone, and/or if the sensing zones are included in, comprise, or are the close contact sensing zones, the respective configurations may be considered to synergistically contribute to the same technical effects.

According to some aspects, the fourth strip element further comprises a printed circuit board. The at least two sensing elements are provided with the printed circuit board so as to be arranged along a longitudinal direction of the printed circuit board. The printed circuit board comprises, in the deformation susceptibility zone, a cutout extending at least partially in a width direction of the printed circuit board, the width direction being a direction perpendicular to the longitudinal direction of the printed circuit board.

A fifth strip element in accordance with the present disclosure is a strip element configured to be internally or externally, fixedly or removably provided to an absorbent hygiene article, such as a diaper. The fifth strip element comprises at least two sensing elements for obtaining excretion-related information in an absorbent hygiene article, such as a diaper. The fifth strip element comprises at least two sensing zones, each of which comprises one of the at least two sensing elements. The two sensing zones are separated by a deformation susceptibility zone that connects the two sensing zones and that is free of any sensing element. The fifth strip element further comprising a printed circuit board. The at least two sensing elements are provided with the printed circuit board so as to be arranged along a longitudinal direction of the printed circuit board. The printed circuit board comprises, in the deformation susceptibility zone, a cutout extending at least partially in a width direction of the printed circuit board, the width direction being perpendicular to the longitudinal direction of the printed circuit board.

The fifth strip element may be configured to be repeatedly attachable to and detachable from a garment facing surface of the absorbent hygiene article.

Optionally, the fifth strip element is any one of the previously described first, second, third, and/or fourth strip elements. The sensing zones may, e.g., be or comprise the close contact sensing zones. The deformation susceptibility zone may, e.g., be or comprise the flex zone.

A longitudinal direction of the printed circuit board may be a direction parallel to a direction of a largest expansion of the printed circuit board. A thickness direction of the printed circuit board may be a direction parallel to a direction of a smallest extension of the printed circuit board. A width direction of the printed circuit board may be a direction perpendicular to the longitudinal direction and also perpendicular to the thickness direction.

Utilizing cutouts as described above may be considered a cost-efficient, yet effective way of providing a strip element with a deformation susceptibility zone. The above-described advantages and/or technical effects associated with the provision of a deformation susceptibility zones may, hence, be achieved in a simple but nevertheless effective way.

According to some aspects, the printed circuit board has, at least in the deformation susceptibility zone, constant thickness. Optionally, the printed circuit board has, in all portions thereof, constant thickness.

Since printed circuit boards having a constant thickness may be associated with cost-efficient manufacturing processes (e.g., when compared to printed circuit boards having varying thicknesses), the above-cited aspects may contribute to lowering cost of manufacturing the strip element.

According to some aspects, the printed circuit board has, at least in the deformation susceptibility zone, flexibility. Put differently, at least parts of the printed circuit board may be flexible printed circuit board ("flex PCB").

Utilizing a printed circuit board having flexibility at least in the deformation susceptibility zones may be considered a cost-efficient and effective way of providing a strip element configured to be internally or externally fixedly or removably provided to an absorbent hygiene article, such as a diaper. Moreover, since a garment facing surface of a hygiene articles such as a diaper may be flexible as well, promoting flexibility of the strip element by using a flexible printed circuit board may further promote wearing comfort of an absorbent hygiene article to which the strip element is attached.

According to some aspects, the flexible printed circuit board comprises at least one of: polyimide; polyester; polytetrafluoroethylene; aramid; and polyethylene naphthalate.

The above-mentioned materials may be associated with mechanical and/or electrical properties contributing to having an optimized amount of flexibility while ensuring compliance with electrical safety requirements.

According to some aspects, the cutout of the fourth strip element or the cutout of the fifth strip element is, in the width direction of the printed circuit board, provided only on one side of the printed circuit board.

A cutout provided only on one side of the printed circuit board may be associated with promoting cost-efficiency of a manufacturing process thereof. That is, if the cutout is manufactured, e.g., by punching and/or cutting the printed circuit board, a small number of punching and/or cutting steps, and/or a small number of punching and/or cutting matrices are needed in order to manufacture the cutout.

According to some aspects, the printed circuit board comprises at least two cutouts provided in the deformation susceptibility zone. The at least two cutouts are, with respect to the width direction of the printed circuit board, arranged in respectively opposite portions of the printed circuit board.

Providing at least two cutouts in respectively opposite portions of the printed circuit board may be associated with the technical effect of promoting torsional flexibility of the strip element comprising the printed circuit board. The torsional flexibility of the strip element may, e.g., be a torsional flexibility with respect to an axis oriented parallel to the longitudinal direction of the printed circuit board. In some cases, the provision of at least two cutouts in respectively opposite portions of the printed circuit board may be associated not only with promoting torsional flexibility (i.e., promoting an increase of torsional flexibility), but also with manipulating a torsional deformation pattern of the strip element. For example, a rather symmetric deformation pattern may be generated due to the provision of tow cutouts in respectively opposite portions of the printed circuit board.

According to some aspects, any one of the previously described fourth or fifth strip elements has a length being defined as the maximum geometrical extension of the strip element, a thickness being defined as an extension of the strip element in direction perpendicular to the length direction, and a width being defined as an extension in a direction perpendicular to the length direction and the thickness direction, respectively. According to these aspects, the width of the strip element in the deformation susceptibility zone is not smaller than the width of the strip element in at least one of, optionally both of, the sensing zones.

A length direction of the strip element may be a direction parallel to a direction of a largest expansion of the strip element. A thickness direction of the strip element may be a direction parallel to a direction of a smallest extension of the strip element. A width direction of the strip element may be a direction perpendicular to the length direction of the strip element and also perpendicular to the thickness direction of the strip element.

It is to be understood that, even if a width of the printed circuit board may vary, e.g., due to the cutouts, a width of the strip element in the deformation susceptibility zone and a width of the strip element in least one of, optionally both of, the sensing zones may be the same. Optionally, the strip element has a constant width at least in a portion in which the sensing zones and the deformation susceptibility zones are provided.

According to an aspect, any one of the previously described fourth or fifth strip elements has a length being defined as the maximum geometrical extension of the strip element, a thickness being defined as an extension of the strip element in direction perpendicular to the length direction, and a width being defined as an extension in a direction perpendicular to the length direction and the thickness direction, respectively. According to these aspects, the thickness of the strip element in the deformation susceptibility zone is not smaller than the thickness of the strip element in at least one of, optionally both of, the sensing zones. Optionally, the strip element has a constant thickness at least in a portion in which the sensing zones and the deformation susceptibility zones are provided.

According to some aspects, the strip element, the second strip element, the third strip element, the fourth strip element and/or the fifth strip element further comprises a sleeve accommodating the at least two sensing elements and optionally also the printed circuit board. The accommodating may take place, e.g., in a cavity of the sleeve. The sleeve may be made of or comprise a silicone-based material, such as silicone rubber. Alternatively or additionally, the sleeve may comprise another polymer-based material having elasticity, such as SEBS, TPE, PUR, or the like. Optionally, the sleeve is liquid proof, i.e., has a configuration preventing a liquid such as water to enter an interior portion of the sleeve so as to get in contact with the sensing elements and/or the printed circuit board.

A sleeve as described above may contribute to a configuration in which the deformation susceptibility zones and/or the flex zones exhibit at least some of their previously described advantages, while simultaneously promoting wearing comfort of an absorbent hygiene article to which the strip element is attached. Moreover, a sleeve as described above may protect components such as the printed circuit board and/or the sensing elements external influences, such as sharp objects and/or liquids.

According to some aspects, the strip element, the second strip element, the third strip element, the fourth strip element and/or the fifth strip element comprises first to third sensing elements, which are provided with the printed circuit board such that the strip element comprises first to fourth sensing zones arranged in a row. Optionally, the first to third sensing zones are further arranged in numerical order. If applicable, the first to third sensing zones may comprise, be included in, or be first to third close contact sensing zones analogously as described above. In the strip element according to these aspects, deformation susceptibility zones and/or flex zones are provided between respectively adjacent sensing zones.

According to some aspects, the strip element, the second strip element, the third strip element, the fourth strip element and/or the fifth strip element comprises first to fourth sensing elements, which are provided with the printed circuit board such that the strip element comprises first to fourth sensing zones arranged in a row. Optionally, the first to third sensing zones are arranged in numerical order. If applicable, the first to fourth sensing zones may be included in, comprise, or be first to fourth close contact sensing zones analogously as described above. In the strip element according to these aspects, deformation susceptibility zones and/or flex zones are provided between respectively adjacent sensing zones.

A strip element comprising at least three or four sensing elements as described above may be associated with the technical effect of promoting increased measurement accuracy. That is, if a third (and/or even a fourth) sensing element is provided in addition to the first and second sensing elements, obtaining information regarding the presence of an excretion may be enabled in at least three (or at least four) portions of the absorbent hygiene article. It may, hence, be possible to determine the presence of an excretion such as urine in the absorbent hygiene article even if the excretion has not been introduced into a portion associated with a location of the first sensing element or the second sensing element. Therefore, it may be less likely to receive a "false negative" measurement result.

Moreover, the presence of more than two sensing elements (e.g., at least three sensing elements or at least four sensing elements) may allow drawing more accurate conclusions as regards a saturation of the absorbent hygiene article. For example, if the first and second sensing elements obtain information indicating that an excretion such as urine is present in a portion associated with the first and second sensing elements, and the third sensing element obtains information indicating that no excretion such as urine is present in a portion associated with the third sensing element, it might not yet be necessary to replace the absorbent hygiene article. Due to the ability to counteract against unnecessary replacement of the absorbent hygiene article, the strip element comprising a third or even a fourth sensing element may be associated with reduced operational cost as well as positive impact on environmental sustainability. Further, it is to be understood that increasing the number of sensing elements may increase a resolution as regards a saturation of the absorbent hygiene article. However, an increased number of sensing elements may also increase manufacturing and/or operational costs (such as costs associated with power supply or the like) of a strip element. Providing three or fourth sensing elements has turned out to be a compromise between receiving enough information so as to draw reliable conclusions as regards a saturation level of the absorbent hygiene article to which the strip element is attached, and not unduly increasing costs of manufacturing and/or operating the strip element.

Moreover, the above-described configuration may allow taking an orientation of a person wearing an absorbent hygiene article to which the strip element is attached into account. That is, if the person (e.g., a newborn or an infant) were to lie on its belly (prone position), a portion to which the excretion such as urine would spread will most likely be different as compared to a state in which the person would lie on its back (supine position). If only a second sensing element were to be provided so as to be on a first side with respect to a first sensing element, the spread of an excretion event such as urine may hardly be detectable as soon as the person were to be in prone position. However, if a third sensing element is provided on an opposite side with respect to the first sensing element (i.e., opposite to the second sensing element), a spread of an excretion event may be monitored in both a prone position and a supine position of the person.

According to some aspects, the printed circuit board of the previously described strip element comprises a cutout in each of the deformation susceptibility zones provided between respectively adjacent sensing zones. According to these aspects, the cutouts are with respect to the width direction of the printed circuit board, provided on alternating sides of the printed circuit board. Optionally, the cutouts are, with respect to the width direction of the printed circuit board, provided only on alternating sides of the printed circuit board. That is, in the latter configuration, a cutout between a first sensing element and a second sensing element provided adjacent to the first sensing element is, with respect to the width direction of the printed circuit board, provided on a first side only, while a cutout between a second sensing element and a third sensing element provided adjacent to the second sensing element is, with respect to the width direction of the printed circuit board, provided on a second side only, the second side opposing the first side. If a fourth sensing element is provided, a cutout between a third sensing element and a fourth sensing element provided adjacent to the third sensing element is, with respect to the width direction of the printed circuit board, provided on the first side only.

A configuration as described above may be associated with the technical effect of promoting ease of shear deformations of the strip element. that is, portions of the strip element corresponding to the sensing elements may, with respect to the width direction of the strip element, be shifted to respectively opposite directions, while not generating significantly high forces with respect to the longitudinal direction of the strip element. This may allow a wearer of an absorbent hygiene article to which the strip element is attached to perform a variety of movements while positions of the sensing elements may, at least in a longitudinal direction of the strip element, not deviate from designated positions thereof.

According to some aspects, a distance between a center of the first sensing element and a center of the second sensing element is between 50 mm and 70 mm. A distance between the center of the second sensing element and a center of the third sensing element is between 30 mm and 50 mm. If a fourth sensing element is provided, a distance between the center of the third sensing element and a center of the fourth sensing element is between 60 mm and 80 mm. The centers of the respective sensing elements may, e.g., be centers of gravity.

The above-described distances may be considered a good compromise between allowing a sufficiently large portion of an absorbent hygiene article to be monitored, and preventing the strip element from having an extension that may significantly impair wearing comfort of a person wearing an absorbent hygiene article to which the strip element is attached.

According to some aspects, the first sensing element, the second sensing element, the third sensing element and/or the fourth sensing elements of the previously described third strip elements, fourth strip elements and/or fifth strip elements may be or comprise sensing elements for measuring an impedance, and/or for measuring a temperature.

According to some aspects, the strip element, the second strip element, the third strip element, the fourth strip element and/or the fifth strip element may comprise a processing module configured to obtain measurement data from the at least two sensing elements. Optionally, the processing module further comprises an energy source such as a battery. The battery may be a rechargeable battery. The strip element may, e.g., further comprise an induction coil for wirelessly charging the battery.

Moreover, according to some aspects, the processing module further comprises a communication module configured to provide an external device with information associated with the measurement data. Optionally, the communication module is a communication module for wirelessly transmitting and/or receiving data. The communication module may, e.g., be a module capable of transmitting and/or receiving data via wireless LAN, Bluetooth, BLE (Bluetooth low energy), GSM, 4G (LTE, Long term evolution), 5G, or the like. The external device may, e.g., a mobile device such as a smartphone or a tablet, a personal computer, or the like.

Further providing a processing module as described above may be considered to reducing the necessity of the strip element being connected to an additional entity (such as connected by wire, the wire being for energy supply and/or data transmission). This configuration may, in turn, lead to improved wearing and operating comfort of the strip element. As regards the provision of an induction coil for wirelessly charging the strip element, a further advantage may lie in that no opening, such as a connector or a flap, is required in order to charge or exchange the battery. The configuration utilizing the induction coil for wirelessly charging the battery may, hence, synergistically contribute to the provision of a liquid-proof sleeve.

According to some aspects, the processing module is arranged adjacent to the first sensing zone. Optionally, a further deformation susceptibility and/or a further flex zone is provided between the first sensing zone and the processing module.

As regards the further deformation susceptibility zone and/or the further flex zone, it is to be understood that the advantages and/or technical effects previously described with respect to the deformation susceptibility zone and/or flex zone apply analogously.

A hygiene system in accordance with the present disclosure comprises an absorbent hygiene article, such as a diaper, and any one of the above-described strip elements, second strip elements, third strip elements and/or fifth strip elements. In the hygiene system, the strip element is attached to a garment facing surface of the absorbent hygiene article. the hygiene system is configured such that no galvanic contact is establishable between any one of the sensing elements and a liquid to be absorbed by the absorbent hygiene article.

The absorbent system may be associated with the same or analogous technical effects and/or advantages as previously described with respect to the strip element, the second strip element, the third strip element, the fourth strip element and/or the fifth strip element.

According to some aspects, the absorbent hygiene article of the absorbent system comprises a first indication means, such as a first print, for indicating, to a user, a first designated location for attaching the strip element to a garment facing surface of the absorbent hygiene article. The first indication means may comprise, e.g., a printed outline provided on a garment facing surface of the absorbent hygiene article, the outline corresponding to the shape of the strip element. Alternatively or additionally, the first indication means may comprise a colored portion of the garment facing surface of the absorbent hygiene article.

Excretion events (such as urinating) in absorbent hygiene articles may start in a particular portion of the absorbent hygiene article, and spread to other portions in case the amount of excretion increases. Considering one and the same user (or a plurality of users of the same age and sex), starting portions of wetness events are often the same portion of the absorbent hygiene article, or corresponding portions of a plurality absorbent hygiene articles. Suggesting a designated location for attaching the strip element to the absorbent hygiene article by virtue of a first indication means may therefore promote a configuration in which a first sensing element is provided in a portion corresponding to a portion where an excretion event usually starts. A second sensing element may be provided, e.g., in a portion to which the excretion (e.g., urine) in the absorbent hygiene article spreads as soon as the amount of excretion increases. The above-described aspects may, hence, aid in promoting measurement accuracy as regards a saturation of the absorbent hygiene article.

According to some aspects, the absorbent hygiene article further comprises a second indication means, such as a second print, for indicating, to a user, a second designated location for attaching the strip element to a garment facing surface of the absorbent hygiene article. The second indication means may comprise, e.g., another printed outline on a garment facing surface of the absorbent hygiene article, the other printed outline also corresponding to the shape of the strip element. Alternatively or additionally, the second indication means may comprise another colored portion of the garment facing surface of the absorbent hygiene article. A color of the second indication means may deviate from a color of the first indication means.

As regards the latter aspects, it is to be understood that starting portions of an excretion event in an absorbent hygiene article may vary depending on a sex of the person wearing the hygiene article. Providing a second indication means as described above may allow taking such variations into account, and may, thus, aid in further promoting measurement accuracy for a larger group of users. The previously discussed aspects may, hence, also be considered to promote flexibility of the absorbent system.

A first method in accordance with the present disclosure is a method of assessing a degree of saturation of an absorbent hygiene article, such as a diaper. According to the first method, the absorbent hygiene is internally or externally, fixedly or removably provided with a strip element, optionally any one of the previously described first to fifth strip elements. The strip element according to the first method comprises at least a first sensing element and a second sensing element. Optionally, the first and second sensing elements are impedance sensing elements for measuring an impedance, respectively. The first method comprises the steps of a first group of steps, the first group including the steps of: detecting a first value from the first sensing element; and detecting a second value from the second sensing element. The first method further comprises at least one step of a second group of steps, the second group including the steps of: assessing that a degree of saturation of the absorbent hygiene article is substantially zero if the first value does not pass a first threshold and the second value does not pass a second threshold; assessing that a first degree of saturation is present in the absorbent hygiene article if the first value passes the first threshold and the second value does not pass the second threshold; assessing that a second degree of saturation is present in the absorbent hygiene article if the first value passes the first threshold and the second value passes the second threshold. The second degree of saturation is a larger degree of saturation than the first degree of saturation. The first method further comprises the steps of a third group of steps, the third group of steps including the step of: outputting a signal indicating a result of an assessing step of the second group of steps.

In the present context, the term "passing" a threshold may relate to exceeding a threshold, i.e., and/or falling below a threshold. An impedance to be measured by an impedance sensing element may, e.g., fall as soon as a liquid such as urine is brought into a vicinity of the impedance sensing element. A temperature to be measured by a temperature sensing element may, e.g., increase as soon as a liquid such as urine is brought into a vicinity of the temperature sensing element.

As an alternative to the above-described second group of steps, the second group of steps of the first method may include the steps of: assessing that a degree of saturation of the absorbent hygiene article is substantially zero if the first value does not pass the first threshold and the second value does not pass the second threshold; assessing that the first degree of saturation is present if exactly one of the first value and the second value passes the respective threshold; assessing that the second degree of saturation is present if each of the first value and the second value pass the respective thresholds;

The first method as described above may allow obtaining not only binary information (i.e., whether an excretion is present in an absorbent hygiene article or not), but also information as regards a saturation of an absorbent hygiene article. When relying upon the first method, one may, hence, be provided with information in order to decide whether the absorbent hygiene article is to be replaced or not, even if the presence of an excretion has been assessed the absorbent hygiene article. For example, if it has been assessed that the first amount of excretion is present in the absorbent hygiene article, it may not be necessary to replace the absorbent hygiene article. If it is, however, assessed that the second amount of excretion is present in the absorbent hygiene article, replacing the absorbent hygiene article may be recommendable. Due to the prevention of unnecessary replacement of the absorbent hygiene article, the first method may be associated with advantages as regards environmental impact and sustainable use of raw materials, as well as cost-related advantages.

According to some aspects, the absorbent hygiene article of the first method is internally or externally, fixedly or removably provided with the strip element comprising at least the first sensing element, the second sensing element, and a third sensing element. Optionally, the first, second and third sensing elements are impedance sensing elements for measuring an impedance, respectively. According to these aspects, the first group of steps further includes the step of detecting a third value from the third sensing element. The second group of steps includes the steps of: assessing that a degree of saturation of the absorbent hygiene article is substantially zero if the first value does not pass the first threshold and the second value does not pass the second threshold and the third value does not pass a third threshold; assessing that the first degree of saturation is present in the absorbent hygiene article if the first value passes the first threshold and the second value does not pass the second threshold and the third value does not pass the third threshold; assessing that the second degree of saturation is present in the absorbent hygiene article if the first value passes the first threshold and either one of the second value and the third value passes the second threshold; assessing that the third degree of saturation is present if the first value passes the first threshold and the second value passes the second threshold and the third value passes the third threshold. The third degree of saturation is a larger degree of saturation than the second degree of saturation.

Alternatively, the second group of steps according to the latter aspects may include the steps of: assessing that a degree of saturation of the absorbent hygiene article is substantially zero if the first value does not pass the first threshold and the second value does not pass the second threshold and the third value does not pass the third threshold; assessing that the first degree of saturation is present if exactly one of the first value, the second value, and the third value passes the respective threshold; assessing that the second degree of saturation is present if exactly two of the first value, the second value, and the third value pass the respective thresholds; assessing that the third degree of saturation is present if each of the first value, the second value, and the third value pass the respective thresholds.

According to some aspects, the absorbent hygiene article of the first method is internally or externally, fixedly or removably provided with a strip element comprising at least the first sensing element, the second sensing element, the third sensing element, and a fourth sensing element. Optionally, the first, second, third, and fourth sensing elements are impedance sensing elements for measuring an impedance.

According to these aspects, the first group of steps further includes the step of detecting a fourth value from the fourth sensing element. The second group of steps includes the steps of: assessing that a degree of saturation of the absorbent hygiene article is substantially zero if the first value does not pass the first threshold and the second value does not pass the second threshold and the third value does not pass the third threshold and the fourth value does not pass a fourth threshold; assessing that the first degree of saturation is present if the first value passes the first threshold and the second value does not pass the second threshold and the third value does not pass the third threshold and the fourth value does not pass the fourth threshold; assessing that the second degree of saturation is present if the first value passes the first threshold and the second value passes the second threshold and the third value does not pass the third threshold and the fourth value does not pass the fourth threshold; assessing that the third degree of saturation is present if the first value passes the first threshold and the second value passes the second threshold and the third value passes the third threshold and the fourth value does not pass the fourth threshold assessing that a fourth degree of saturation is present if the first value passes the first threshold and the second value passes the second threshold and the third value passes the third threshold and the fourth value passes the fourth threshold. The fourth degree of saturation is a larger degree of saturation than the third degree of saturation.

Alternatively, the second group of steps according to the latter aspects may include the steps of: assessing that a degree of saturation of the absorbent hygiene article is substantially zero if the first value does not pass the first threshold and the second value does not pass the second threshold and the third value does not pass the third threshold and the fourth value does not pass a fourth threshold; assessing that the first degree of saturation is present if exactly one of the first value, the second value, the third value and the fourth value passes the respective threshold; assessing that the second degree of saturation is present if exactly two of the first value, the second value, the third value and the fourth value pass the respective thresholds; assessing that the third degree of saturation is present if exactly three of the first value, the second value, the third value and the fourth value pass the respective thresholds; and assessing that a fourth degree of saturation is present if each of the first value, the second value, the third value and the fourth value pass the respective thresholds.

Utilizing three or four sensing elements as described above may be associated with the technical effect of promoting increased measurement accuracy. That is, if a third (and/or even a fourth) sensing element is provided in addition to the first and second sensing elements, obtaining information regarding the presence of an excretion may be enabled in at least three (or at least four) portions of the absorbent hygiene article. It may, hence, be possible to determine the presence of an excretion such as urine in the absorbent hygiene article even if the excretion has not been introduced into a portion associated with a location of the first sensing element or the second sensing element. Therefore, it may be less likely to receive a "false negative" measurement result.

According to some aspects, the first sensing element is arranged between the second sensing element and the third sensing element. Optionally, the strip element may be provided, as seen in a longitudinal direction thereof, with one of the second and third sensing elements, the first sensing element, and the other one of the second and third sensing elements, in the stated order. A longitudinal direction of the strip element may be a direction corresponding to the largest extension of the strip element. If the strip element is bendable and/or follows a curve in a longitudinal direction thereof, the strip element may be provided, along the curve, with one of the second and third sensing elements, the first sensing element, and the other one of the second and third sensing elements, in the stated order.

A configuration in which the first sensing element is provided between the second sensing element and the third sensing element may allow taking an orientation of a person wearing an absorbent hygiene article to which the strip element is attached into account. That is, if the person (e.g., a newborn or an infant) were to lie on its belly (prone position), a portion to which the excretion such as urine would spread (e.g., while the saturation of the absorbent hygiene article increases) will most likely be different as compared to a state in which the person would lie on its back (supine position). If only a second sensing element were to be provided so as to be on a first side with respect to a first sensing element, the spread of an excretion event such as urine may hardly be detectable as soon as the person were to be in prone position. However, if the first sensing element is provided between the second and third sensing element, a spread of an excretion event (i.e., an increase in saturation of the absorbent hygiene article) may be monitored in both a prone position and a supine position of the person.

According to some aspects, the first threshold is set such that the first value passes the first threshold as soon as liquid such as urine has migrated through an absorbent core of the absorbent hygiene article in a portion corresponding to the first sensing element. Alternatively or additionally, the second threshold may be set such that the second value passes the second threshold as soon as liquid such as urine has migrated through an absorbent core of the absorbent hygiene article in a portion corresponding to the second sensing element. Alternatively or additionally, the third threshold may be set such that the third value passes the third threshold as soon as liquid such as urine has migrated through an absorbent core of the absorbent hygiene article in a portion corresponding to the third sensing element. Alternatively or additionally, the fourth threshold may be set such that the fourth value passes the fourth threshold as soon as liquid such as urine has migrated through an absorbent core of the absorbent hygiene article in a portion corresponding to the fourth sensing element.

According to the latter aspects, accuracy of a detection result of the first method may be promoted.

According to some aspects, any one of the above-described first method may further comprise an initializing group of steps. Optionally, the initializing group of steps is conducted prior the first group of steps. The initializing group of steps comprises the step of detecting an orientation value from an orientation sensing element of the strip element and/or detecting an acceleration value from an acceleration sensing element of the strip element.

According to some aspects, the initializing group of steps further comprises the step of setting at least one of the first threshold, the second threshold, the third threshold, and the fourth threshold, based on the detected orientation value and/or the acceleration value.

Excretion such as urine may spread quite differently in an absorbent hygiene article depending on a movement (e.g., running, sitting, jumping) of a person wearing the absorbent hygiene article. Likewise, excretion such as urine may spread quite differently in an absorbent hygiene article depending on an orientation (e.g., standing, sitting, lying in prone position, or lying supine position) of a person wearing the absorbent hygiene article. Taking an orientation value and/or an acceleration value into account when setting the respective thresholds may, hence, aid in promoting measurement accuracy.

According to some aspects, the initializing group of steps further comprises the step of: activating a stand-by mode if the motion value and/or acceleration value is within a stand-by range of values; and/or the step of deactivating a stand-by mode if the motion value and/or acceleration value is within an activity range of values.

According to the latter aspects, an average energy consumption of the sensing elements may be reduced. Reduced energy consumption may, in turn, be associated with reduced costs and/or environmental advantages such as reduced carbon dioxide emissions. Moreover, if the strip element utilizes a rechargeable battery, a charging interval of the strip element may be increased, thus, promoting convenience of use.

According to some aspects, the first and second groups of steps are conducted in the stated order. According to some aspects, the first group of steps, the second group of steps and the outputting group of steps are conducted in the stated order. According to some aspects, the first, second and third groups of steps are conducted in the stated order. According to some aspects, the first group of steps, the second group of steps, the third group of steps and the outputting group of steps are conducted in the stated order. According to some aspects, the initializing group of steps, the first group of steps, and the second group of steps are conducted in the stated order. According to some aspects, the initializing group of steps, the first group of steps, the second group of steps and the outputting group of steps are conducted in the stated order. According to some aspects, the initializing group of steps, the first group of steps, the second group of steps, and the third group of steps are conducted in the stated order. According to some aspects, the initializing group of steps, the first group of steps, the second group of steps, the third group of steps and the outputting group of steps are conducted in the stated order.

According to some aspects, the strip element is attached to a garment facing surface of the absorbent hygiene article. Optionally, strip element is provided such that no galvanic contact is establishable between the sensing elements of the strip element and an excretion such as urine.

A strip element being attached to a garment facing surface of the absorbent hygiene article may be associated with advantages regarding hygiene. That is, in contrast to configurations in which the strip element is provided, e.g., in a cavity of an absorbent material of the absorbent hygiene article, the strip element will most likely not be in direct contact with an excretion if it is attached to a garment facing surface of the absorbent hygiene article. Consequently, the strip element does not necessarily need to be cleaned or replaced on a regular basis.

A sixth strip element in accordance with the present disclosure is a strip element configured to carry out any one of the above-described methods. The sixth strip element may be configured to be repeatedly attachable and detachable from a garment facing surface of the absorbent hygiene article. The sixth strip element may be any one of the first to fifth strip elements.

The above-described sixth strip element may be associated with the same or analogous advantages and/or technical effects as previously described with respect to the first method and/or the first to fifths strip elements.

A second method in accordance with the present disclosure is a method of distinguishing between no excretion, a first type of excretion, and a second type of excretion in an absorbent hygiene article, such as a diaper. According to the second method, the absorbent hygiene article is internally or externally, fixedly or removably provided with a strip element, optionally any one of the previously described first to sixth strip elements. The strip element comprises a first temperature sensing element for detecting a temperature, and a first impedance sensing element for detecting an impedance. The second method comprises the steps of a first group of steps, the first group including the steps of: detecting a first temperature value with the first temperature sensing element; and detecting a first impedance value with the first impedance sensing element. The second method further comprises at least one step of a second group of steps, the second group including the steps of: determining that no excretion is present in a first portion of the absorbent hygiene article if the first temperature value does not pass a first temperature threshold and the first impedance value does not pass a first impedance threshold; determining that a first type of excretion is present in the first portion of the absorbent hygiene article if the first temperature value passes the first temperature threshold and the first impedance value passes the first impedance threshold; determining that a second type of excretion is present in the first portion of the absorbent hygiene article if the first temperature value passes the first temperature threshold and the first impedance value does not pass the first impedance threshold.

It is to be understood that, while performing measurement, neither of an impedance sensor or a temperature sensor may need to establish galvanic contact to an excretion of an absorbent hygiene article. The above-described second method may, hence, not only allow distinguishing between types of excretion, but even allow distinguishing between types of excretion without needing to establish galvanic contact to the respective excretion. Consequently, the strip element utilized in the second method does not necessarily need to be cleaned or replaced on a regular basis.

According to some aspects, the second method further comprises the steps of an outputting group of steps, the outputting group of steps including the step of outputting a signal indicating a result of a determining step of the second group of steps.

A step of outputting a signal may, in the first method and/or in the second method in accordance with the present disclosure, comprise: sending a signal via a wireless or wired connection to an external device such as a smartphone; an optical output such as a light; and/or an acoustic output such as a beeping sound or the like. The strip element may comprise an illuminator such as an LED-light or the like, and/or a sound generator such as a speaker or the like.

According to some aspects, the strip element of any one of the previously described second methods further comprises a second impedance sensing element for detecting an impedance. The first group of steps further comprises the steps of: detecting a second impedance value with the second impedance sensing element. The method further comprises at least one step of a third group of steps, the third group of steps including the steps of: determining that no excretion is present in a second portion of the absorbent hygiene article if the first temperature value does not pass a second temperature threshold and the second impedance value does not pass a second impedance threshold; determining that a first type of excretion is present in the second portion of the absorbent hygiene article if the first temperature value passes the second temperature threshold and the second impedance value passes the second impedance threshold; determining that a second type of excretion is present in the second portion of the absorbent hygiene article if the first temperature value passes the second temperature threshold and the second impedance value does not pass the second impedance threshold. The method further comprises the steps of an outputting group of steps, the outputting group of steps including the step of: outputting a signal indicating a result of a determining step of the second group of steps and/or of the third groups of steps.

According to some aspects, the strip element of any one of the previously described second methods further comprises a second impedance sensing element for detecting an impedance, and a second temperature sensing element for detecting a temperature. The first group of steps further comprises the steps of: detecting a second impedance value with the second impedance sensing element; and detecting a second temperature value with the second temperature sensing element. The method further comprising at least one step of a third group of steps, the third group of steps including the steps of: determining that no excretion is present in a second portion of the absorbent hygiene article if the second temperature value does not pass a second temperature threshold and the second impedance value does not pass a second impedance threshold; determining that a first type of excretion is present in the second portion of the absorbent hygiene article if the second temperature value passes the second temperature threshold and the second impedance value passes the second impedance threshold; determining that a second type of excretion is present in the second portion of the absorbent hygiene article if the second temperature value passes the second temperature threshold and the second impedance value does not pass the second impedance threshold. The method further comprises the steps of an outputting group of steps, the outputting group of steps including the step of: outputting a signal indicating a result of a determining step of the second group of steps and/or of the third groups of steps.

According to the latter aspects, the previously described advantages of distinguishing between types of excretion may be combined with the advantages of determining an amount of excretion present in the absorbent hygiene article and/or a saturation of the absorbent hygiene article. The latter aspects, hence, synergistically contribute to generating a rather accurate representation of a situation present in an absorbent hygiene. An accurate representation may, in turn, provide sufficient information in order to determine whether an absorbent hygiene article needs to be replaced or not. The latter information may, in particular, allow taking both environmental aspects such as a generation of waste, and aspects relating to wearing comfort of an absorbent hygiene article potentially accommodating an excretion into account on a rather precise basis.

According to some aspects, the first type of excretion is urine, and/or the second type of excretion is feces.

According to some aspects, the first impedance sensing element and the first temperature sensing element are provided in a first portion of the strip element, and the second impedance sensing element and the second temperature sensing element are provided in a second portion of the strip element. Optionally, a distance between the first temperature sensing element and any one of the second temperature sensing element and the second impedance sensing element is larger than a distance between the first temperature sensing element and the first impedance sensing element. Alternatively or additionally, a distance between the first impedance sensing element and any one of the second temperature sensing element and the second impedance sensing element is larger than a distance between the first temperature sensing element and the first impedance sensing element.

According to some aspects, the second group of steps of any one of the previously described second methods further includes the step of determining that an external interference and/or a measurement error is present in the first portion of the absorbent hygiene article if the first temperature value does not pass the first temperature threshold and the first impedance value passes the first impedance threshold. Alternatively or additionally, the third group of steps of any one of the previously described second methods further includes the step of determining that an external interference and/or a measurement error is present in the second portion of the absorbent hygiene article if the first or second temperature value does not pass the first temperature threshold and the second impedance value passes the first impedance threshold.

Further determining the presence of an external interference and/or a measurement error may allow timely recognizing a state in which the strip element should be replaced, repaired and/or put to maintenance. The previously described aspects may, hence, aid in preventing measurement errors, e.g., due to a defective strip element.

According to some aspects, any one of the previously described first or second methods comprises all steps of the respective second group of steps.

According to some aspects, any one of the previously described first or second methods comprises all steps of the respective third group of steps.

According to some aspects, any one of the above-described second methods further comprises an initializing group of steps. Optionally, the initializing group of steps is conducted prior the first group of steps. The initializing group of steps comprises the step of detecting an orientation value from an orientation sensing element of the strip element and/or detecting an acceleration value from an acceleration sensing element of the strip element.

According to some aspects, the initializing group of steps further comprises the step of setting at least one of the first temperature threshold, the second temperature threshold, the first impedance threshold, and the second impedance threshold based on the detected orientation value and/or the acceleration value.

Excretion such as urine may spread quite differently in an absorbent hygiene article depending on a movement (e.g., running, sitting, jumping) of a person wearing the absorbent hygiene article. Likewise, excretion such as urine may spread quite differently in an absorbent hygiene article depending on an orientation (e.g., standing, sitting, lying in prone position, or lying supine position) of a person wearing the absorbent hygiene article. Taking an orientation value and/or an acceleration value into account when setting the respective thresholds may, hence, aid in promoting measurement accuracy.

According to some aspects, the initializing group of steps further comprises the step of: activating a stand-by mode if the motion value and/or acceleration value is within a stand-by range of values; and/or the step of deactivating a stand-by mode if the motion value and/or acceleration value is within an activity range of values.

According to the latter aspects, an average energy consumption of the sensing elements may be reduced. Reduced energy consumption may, in turn, be associated with reduced costs and/or environmental advantages such as reduced carbon dioxide emissions. Moreover, if the strip element utilizes a rechargeable battery, a charging interval of the strip element may be increased, thus, promoting convenience of use.

According to some aspects, the first and second groups of steps are conducted in the stated order. According to some aspects, the first group of steps, the second group of steps and the outputting group of steps are conducted in the stated order. According to some aspects, the first, second and third groups of steps are conducted in the stated order. According to some aspects, the first group of steps, the second group of steps, the third group of steps and the outputting group of steps are conducted in the stated order. According to some aspects, the initializing group of steps, the first group of steps, and the second group of steps are conducted in the stated order. According to some aspects, the initializing group of steps, the first group of steps, the second group of steps and the outputting group of steps are conducted in the stated order. According to some aspects, the initializing group of steps, the first group of steps, the second group of steps, and the third group of steps are conducted in the stated order. According to some aspects, the initializing group of steps, the first group of steps, the second group of steps, the third group of steps and the outputting group of steps are conducted in the stated order.

According to some aspects, the strip element utilized in the second method is attached to a garment facing surface of the absorbent hygiene article such that no galvanic contact is established between excretion and the first and/or second impedance sensing element, and also between the excretion and the first and/or second temperature sensing element while carrying out the second method. Optionally, strip element is provided and/or configured such that no galvanic contact is establishable between the sensing elements of the strip element and an excretion such as urine. A configuration in which no galvanic contact is establishable between the sensing elements of the strip element and an excretion such as urine may utilize, e.g., a sleeve of the strip element accommodating the strip element in a liquid proof manner.

A strip element being attached to a garment facing surface of the absorbent hygiene article may be associated with advantages regarding hygiene. That is, in contrast to configurations in which the strip element is provided, e.g., in a cavity of an absorbent material of the absorbent hygiene article, the strip element will most likely not be in direct contact with an excretion if it is attached to a garment facing surface of the absorbent hygiene article. Consequently, the strip element does not necessarily need to be cleaned or replaced on a regular basis.

A seventh strip element in accordance with the present disclosure is a strip element configured to carry out any one of the above-described second methods. The seventh strip element may be configured to be repeatedly attachable and detachable from a garment facing surface of the absorbent hygiene article. Moreover, the seventh strip element may be any one of the previously described first to sixth strip elements.

The seventh strip element may be associated with the same or analogous advantages and/or technical effects as previously described with respect to the first method and/or the first to fifths strip elements.

Moreover, it is to be noted that a strip element configured to be repeatedly attachable and detachable from a garment facing surface of an absorbent hygiene article may be associated with the technical effect of promoting ease of re-use.

Preferably, the strip element, the second strip element, the fourth strip element, the fifth strip element, the sixth strip element and/or the seventh strip elements is configured to be externally and removably provided to an absorbent hygiene article.

An advantage of the strip element being configured to be removable may reside in a reusability of the strip element. In this regard, it is to be noted that the reusability of the strip element may be promoted despite a disposable nature of the absorbent product. An advantage of the strip element being configured to be externally provided to the absorbent hygiene article may lie in that there is no need to integrate electronic/metallic components into the absorbent product. Moreover, the removability and the external provision may synergistically contribute to promoting ease of cleaning of the strip element.

BRIEF DESCRIPTION OF THE DRAWINGS

Additional advantages and features of the present disclosure, that can be realized on their own or in combination with one or several features discussed above, insofar as the features do not interfere with each other, will become apparent from the following description of working examples and/or optional aspects and/or embodiments. The description is provided with reference to the accompanying drawings, in which.

DETAILED DESCRIPTION OF EMBODIMENTS

Embodiments of devices, uses and methods in accordance with the present disclosure will hereinafter be explained in detail, by way of non-limiting example only, and with reference to the accompanying drawings. Like reference signs appearing in different figures denote identical, corresponding, or functionally similar elements, unless indicated otherwise.

Figure 1A:
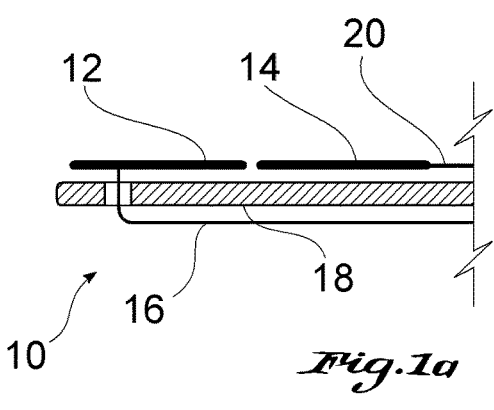
FIG. 1a is a schematic cross-sectional view of a sensing element of an embodiment of a strip element in accordance with the present disclosure.
Figure 2A:
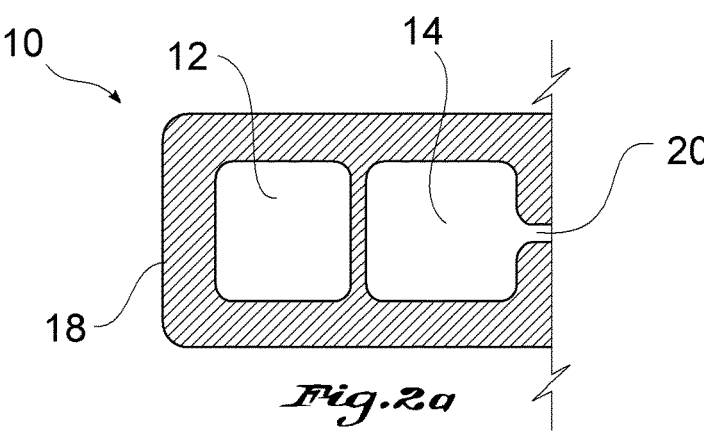
FIG. 2a is a top view of a sensing element of an embodiment of a strip element in accordance with the present disclosure.

FIG. 1a is a schematic cross-sectional view of a sensing element 10 of an embodiment of a strip element 40 in accordance with the present disclosure. FIG. 2a is a top view of a sensing element 10 of an embodiment of a strip element 40 in accordance with the present disclosure. The sensing element of FIG. 1a and the sensing element of FIG. 2a may be the same sensing element. The sensing element 10 of FIG. 1a and FIG. 2a is a sensing element for measuring an impedance. The sensing element 10 has a capacitor electrode 12, a signal line 16, and a ground element. The ground element comprises a ground electrode 14 and a ground line 20 electrically connected thereto. The capacitor electrode 12 is electrically connected to the signal line 18. The sensing element 10 further comprises a shielding component 18 provided between the signal line 16 and the ground element comprising the ground electrode 14 and the ground line 20. The strip element 40 according to depicted embodiment is configured such that an electric potential of the shielding component 18 synchronously oscillates with an electric potential of the signal line 16. In this regard, it is to be understood that, since the signal line 16 and the capacitor electrode 12 are electrically connected to each other, an electric potential of the capacitor electrode 12, an electric potential of the signal line 16, and an electric potential of the shielding component 18 oscillate synchronously. Each of the capacitor electrode 12, the ground electrode 14, the signal line 16, the shielding component 18 and the ground line 20 may be made of electrically conductive material such as metal. The shielding component 18 may, e.g., be made of or comprise copper or a copper alloy. The capacitor electrode 12 and the signal line 16 are electrically insulated from the shielding component 18, the ground electrode 14 and the ground line 20. The shielding component 18 is electrically insulated from the capacitor electrode 12, the signal line 16, the ground electrode 14, and the ground line 20. According to the depicted embodiment, the capacitor electrode 12, the ground electrode 14 and the ground line 20 are provided in a first layer of the sensing element 10. The shielding component 18 is provided in a second layer of the sensing element 10, the second layer being provided below the first layer. The signal line 16 starts from the first layer, runs through the second layer, and is then provided in a first layer of the sensing element 10 provided below the second layer. When running through the second layer, the signal line 16 is guided through an opening of the shielding component 18 such that no electrical contact is establishable between the shielding component 18 and the signal line 16. Even though no insulating layers are depicted in FIG. 1a or FIG. 2a, a first insulating layer may be provided between the first layer and the second layer, and a second insulating layer may be provided between the second layer and the third layer. The first and second insulating layers may each comprise an opening, a position of which corresponds to the position of the opening of the shielding component 18. In the depicted embodiment, the capacitor electrode 12 is provided adjacent to the ground electrode 14. Moreover, in the depicted embodiment, each of the capacitor electrode 12 and the ground electrode 14 has a substantially rectangular shape. In the sensing elements 10 depicted in FIGS. 1a and 2a, the shielding component 18 is continuously provided between the ground element and the signal line 16 such that there is no portion of the sensing element 10 in which the shielding component 18 is not provided between the ground element and the signal line 16. The ground element includes the ground electrode 14 and the ground line 20.

Figure 1B:
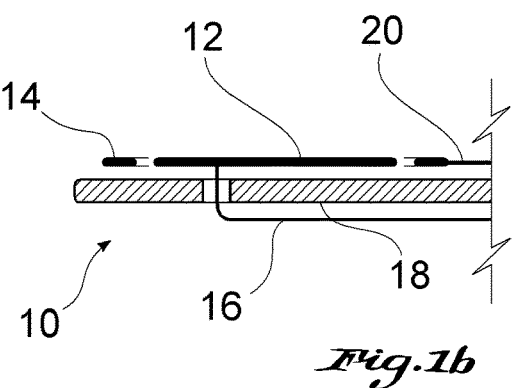
FIG. 1b is a schematic cross-sectional view of a sensing element of an embodiment of a strip element in accordance with the present disclosure.
Figure 2B:
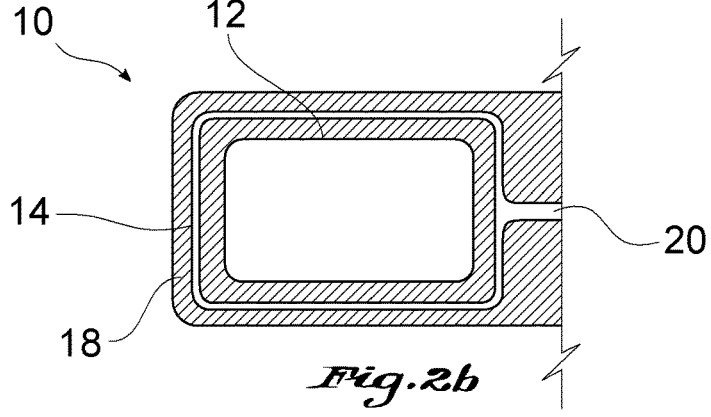
FIG. 2b is a top view of a sensing element of an embodiment of a strip element in accordance with the present disclosure.

FIG. 1b is a schematic cross-sectional view of a sensing element 10 of an embodiment of a strip element 40 in accordance with the present disclosure. FIG. 2b is a top view of a sensing element 10 of an embodiment of a strip element 40 in accordance with the present disclosure. The sensing element of FIG. 1b and the sensing element of FIG. 2b may be the same sensing element 10. The configuration of the sensing element 10 depicted in FIG. 1b substantially corresponds to the configuration of the sensing element 10 of FIG. 1a, however, in the sensing element 10 of FIG. 1b, the ground electrode 14 is provided so as to form a closed loop around the capacitor electrode 12. In other words, the ground electrode 14 depicted in FIG. 1b surrounds the capacitor electrode 12 of the sensing element 10 of FIG. 1b. Likewise, the configuration of the sensing element 10 depicted in FIG. 2b substantially corresponds to the configuration of the sensing element 10 of FIG. 2a, however, in the sensing element 10 of FIG. 2b, the ground electrode 14 is provided so as to form a closed loop around the capacitor electrode 12. In other words, the ground electrode 14 depicted in FIG. 2b surrounds the capacitor electrode 12 of the sensing element 10 of FIG. 2b.

In the sensing elements 10 depicted in FIGS. 2a and 2b, the respective shielding components 18 are continuously provided between the respective ground elements (including the respective ground electrodes 12 and the respective ground lines 20), and the respective signal lines 18, such that there is no portion of the sensing elements 10 in which the respective shielding component 18 is not provided between the ground element and the signal line 16. Moreover, in the sensing elements 10 depicted in FIGS. 2a and 2b, the respective shielding components 18 are provided so as to extend, with respect to width directions and longitudinal directions of the sensing elements 10, beyond an outline of the respective capacitor electrodes 12, and also beyond an outline of the respective ground electrodes 14. In the present context, a thickness direction of the sensing element 10 is a direction corresponding to a smallest extension of the sensing element. A longitudinal direction is a direction corresponding to a largest extension of a sensing element. A width direction of the sensing element may be a direction perpendicular to the longitudinal direction of the sensing element, and also to the thickness direction of the sensing element.

Figure 2C:
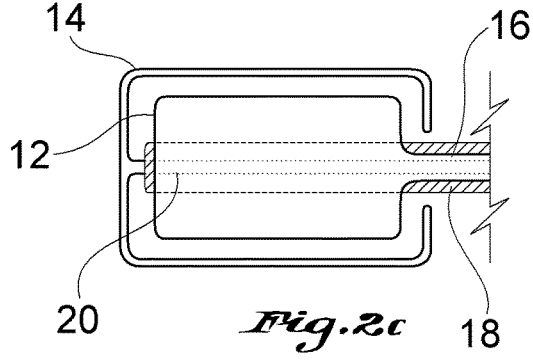
FIG. 2c is a top view of a sensing element of an embodiment of a strip element in accordance with the present disclosure.

FIG. 2c is a top view of a sensing element 10 of an embodiment of a strip element in accordance with the present disclosure. The sensing element 10 of FIG. 2c may correspond to the sensing element of FIG. 2b, but at least the following aspects may differ from the sensing element 10 of FIG. 2c: Firstly, the signal line 16 of the capacitor electrode 12 is provided in the same layer as the capacitor electrode 12. Secondly, the ground line 20 is provided so as to run below the capacitor electrode 12. Thirdly, the ground electrode 14 is provided so as to form an open loop around the capacitor electrode 12. That is, a break is provided in the ground electrode 14 in a portion corresponding to the signal line 16 in order to let the signal line 16 pass therethrough. The signal line 16 may, hence, be guided from an interior portion of the loop to an exterior portion of the loop without needing to change its layer. The shielding component 18 is provided between the capacitor electrode 12 and the ground line 20, however, the shielding component 18 does not extend, with respect to width directions and longitudinal directions of the sensing elements 10, beyond an outline of the ground electrode 14.

Figures 3, 4:
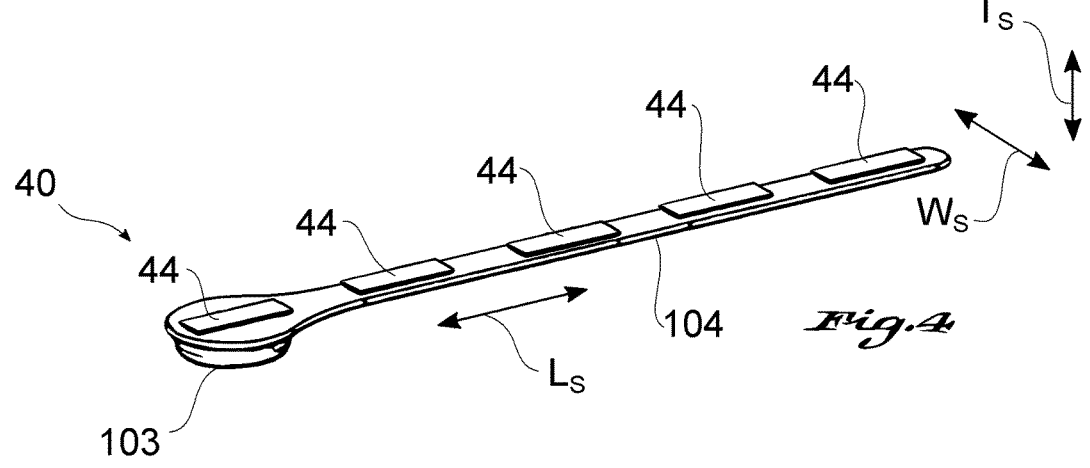
FIG. 3 is a perspective exploded view of an embodiment of a strip element in accordance with the present disclosure.
FIG. 4 is a perspective view of an embodiment of a strip element in accordance with the present disclosure.

FIG. 3 is a perspective exploded view of an embodiment of a strip element 40 in accordance with the present disclosure. The strip 40 element comprises an upper lid 102 and a lower lid 103, which may be put together in a liquid proof manner so as to form a sleeve for accommodating components of the strip element 40 in an interior portion thereof. Components to be accommodated in an interior portion of the sleeve are: a flexible printed circuit board (flex PCB) 50 comprising four sensing elements 42; and a processing unit assembly. The four sensing elements 42 may, e.g., the sensing elements of any one of FIGS. 1a, 1b, 2a, 2b, 2c. The processing unit assembly may comprise: a processing unit printed circuit board 56, which may, e.g., a rigid printed circuit board; a battery 52 electrically connected to the processing unit printed circuit board 56. The battery 52 may further be mechanically attached to the processing unit printed circuit board via a battery tape 54. The processing unit may further comprise an upper hard cover 58 and a lower hard cover 60, forming a processing unit hard case configured to accommodate the processing unit printed circuit board 58 to which the battery 52 is attached. The processing unit upper hard cover 58 may be or comprise polymer-based material such as polypropylene, polybutylenetherephtalate, or the like. The processing unit lower hard cover 60 may be or comprise polymer-based material such as polypropylene, polybutylenetherephtalate, or the like. In the embodiment depicted in FIG. 4, the lower lid 103 has a processing unit accommodating portion 105 and a flexible printed circuit board 50 accommodating portion 104. The flexible printed circuit board 50 accommodating portion 104 has a smaller width than the processing unit accommodating portion. In FIG. 3, a longitudinal direction of the printed circuit board 50 is indicated by reference sign $L_{PCB}$, a width direction of the printed circuit board 50 is indicated by reference sign $W_{PCB}$, a thickness direction of the printed circuit board 50 is indicated by reference sign $T_{PCB}$. The flexible printed circuit board 50 comprises deformation susceptibility zones arranged between respectively two sensing elements 42. In the depicted embodiment, each of the deformation susceptibility zones comprises a cut-out 48. That is, a cut-out 48 is provided between respectively two sensing elements 42, with respect to a longitudinal direction L of the strip element 40. Moreover, the cut-outs 48 are provided in respectively opposite portions of the printed circuit board 50, with respect to the width direction W.

The printed circuit board 50 of the strip element 40 may be connected to the upper lid 102, e.g., by virtue of FPC tape (flexible printed circuit board tape). Attachment portions for attaching the printed circuit board 50 to the upper lid 102 may correspond to portions of the sensing elements 42. According to the latter configuration, a configuration may be promoted in which the sensing elements 42 are provided close to a surface of an absorbent hygiene article, such as a diaper. The latter configuration may, in turn, aid in promoting measurement accuracy of the sensing elements.

The upper lid 102 of the strip element 40 is provided with hook fasteners 44 for repeatedly attaching and detaching the strip element to a garment facing surface of the absorbent hygiene article. In the depicted embodiment, hook fasteners 44 are provided in portions corresponding to portions of the sensing elements 42, thereby forming close contact sensing zones.

FIG. 4 is a perspective view of an embodiment of a strip element 40 in accordance with the present disclosure. FIG. 4 may be considered to depict the strip element 40 of FIG. 3 in an assembled state. The strip element 40 of FIG. 4, may, hence, comprise all components depicted in FIG. 3. In FIG.

4, a longitudinal direction of the strip element 40 is indicated by reference sign $L_S$; a width direction of the strip element 40 is indicated by reference sign $W_S$; a thickness direction of the strip element 40 is indicated by reference sign $T_S$.

Figure 5:
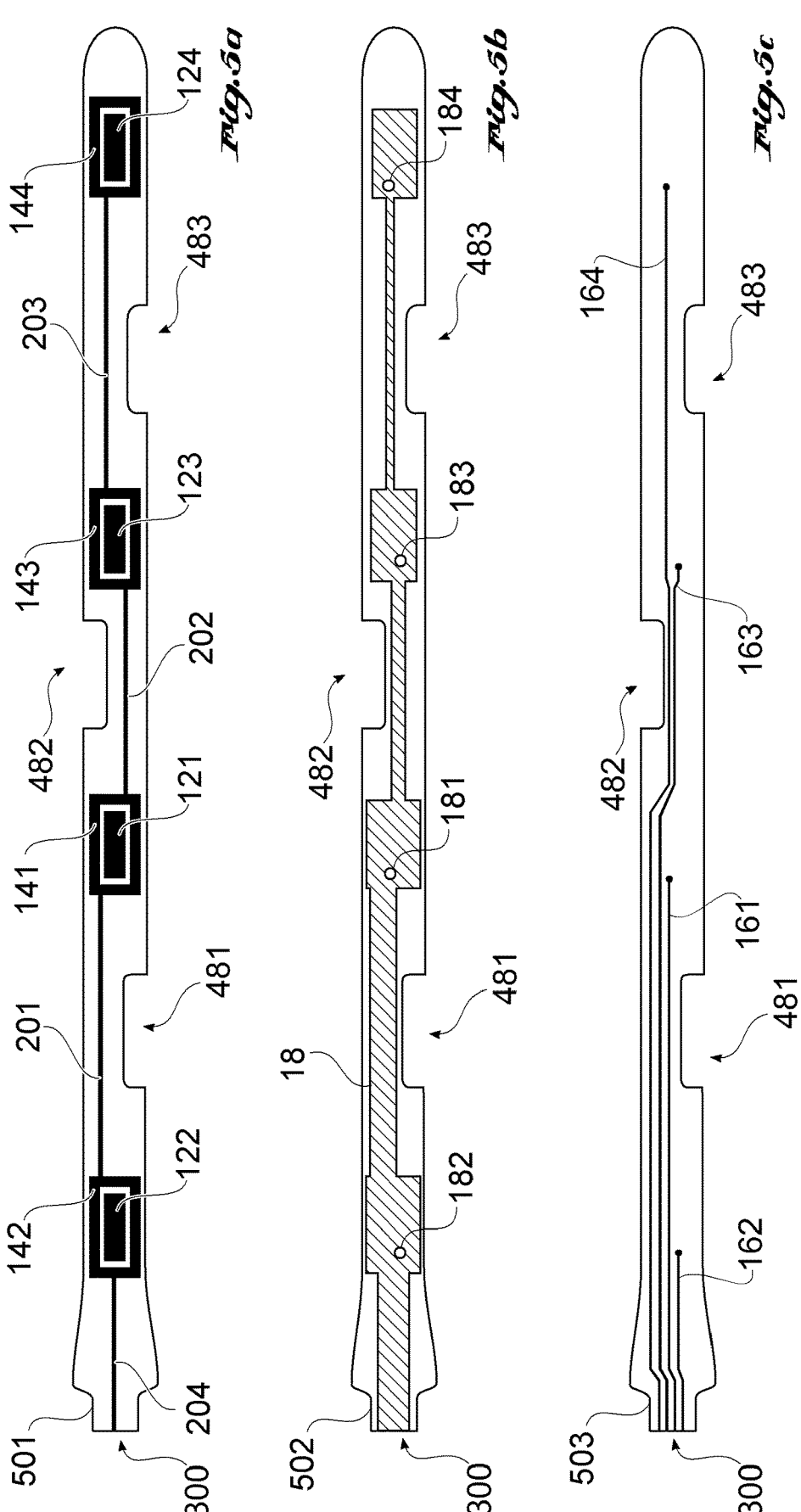
FIG. 5a is a top view of a first layer of a flexible printed circuit board of an embodiment of a strip element in accordance with the present disclosure.
FIG. 5b is a top view of a second layer of a flexible printed circuit board of an embodiment of a strip element in accordance with the present disclosure.
FIG. 5c is a top view of a third layer of a flexible printed circuit board of an embodiment of a strip element in accordance with the present disclosure.

FIG. 5a is a top view of a first layer 501 of a flexible printed circuit board of an embodiment of a strip element in accordance with the present disclosure. FIG. 5b is a top view of a second layer 502 of a flexible printed circuit board of an embodiment of a strip element in accordance with the present disclosure. FIG. 5c is a top view of a third layer 503 of a flexible printed circuit board of an embodiment of a strip element in accordance with the present disclosure. The first layer 501 of FIG. 5a, the second layer 502 of FIG. 5b, and the third layer 503 of FIG. 5c are layers of the same printed circuit board. The first layer 501 of FIG. 5a, the second layer 502 of FIG. 5b, and the third layer 503 of FIG. 5c may be stacked in numerical order. It is, however, to be understood that the printed circuit board, layers of which are depicted in FIGS. 5a to 5c, may comprise more layers than the depicted layers. The layers depicted in FIGS. 5a to 5c may be layers of the printed circuit board 50 depicted in FIG. 3.

The first layer 501 depicted in FIG. 5a comprises a first capacitor electrode 121 of a first sensing element, a second capacitor electrode 122 of a second sensing element, a third capacitor electrode 123 of a third sensing element, and a fourth capacitor electrode 124 of a fourth sensing element. The first sensing element is provided in-between the second sensing and the third sensing element. The first layer 501 further comprises a first ground electrode 141 of the first sensing element, a second ground electrode 142 of the second sensing element, a third ground element 143 of the third sensing element and a fourth ground electrode 144 of the fourth sensing element. The first ground electrode 141 is electrically connected to the second ground electrode 142 by a first ground line 201. The fourth ground electrode 144 is electrically connected to the third ground electrode 143 by the third ground line 203. The third ground electrode 143 is electrically connected to the first ground electrode 141 by the second ground line 142. The second ground electrode 142 is electrically connectable to a processing unit to be provided at a connector end 300 of the flexible printed circuit board, by a fourth ground line 204. In order to form deformation susceptibility zones, the first layer 501 comprises: a first cut-out 481 provided between the first sensing element and the second sensing element; a second cut-out 482 provided between the first sensing element and the third sensing element; a third cut-out 483 provided between the third sensing element and the fourth sensing element.

The second layer 502 depicted in FIG. 5b comprises the shielding component 18. In the depicted case, the shielding component 18 is arranged so as to be provided below the first capacitor electrode 121, the second capacitor electrode 122, the third capacitor electrode 123, and the fourth capacitor electrode 124. Moreover, the shielding component 18 is arranged so as to be at least partially provided below the first ground electrode 141, the second ground electrode 142, the third ground electrode 143, and the fourth ground electrode 144. Moreover, the shielding component 18 is arranged so as to be provided below the first ground line 201, the second ground line 202, the third ground line 203, and the fourth ground line 204. Each of the first to fourth sensing elements share one and the same shielding component 18. An electric potential of the shielding component 18 of the first to fourth sensing element, an electric potential of the first capacitor electrode 122, an electric potential of the second capacitor electrode 142, an electric potential of the third capacitor electrode 143, and an electric potential of the fourth capacitor electrode 144 oscillate synchronously. Portions of the shielding component 18 corresponding to the portions of the capacitor electrodes 121, 122, 123, 124 respectively comprise openings 181, 182, 183, 184 for electrically connecting the capacitor electrodes 141, 142, 143, 144 to signal lines 161, 162, 163, 164 of the third layer 503 depicted in FIG. 5c. In order to form deformation susceptibility zones, also the second layer 502 comprises the first cut-out 481, the second cut-out 482, and the third cut-out 483. As the first cut-out 481, the second cut-out 482, and the third cut-out 483 are cut-outs of the flexible printed circuit board comprising the first layer 501, the second layer 502, and the third layer 503, the positions of the cut-outs of the respective layers are congruent.

The third layer 503 depicted in FIG. 5c comprises signal lines 161, 162, 163, 164. The first signal line 161 is electrically connected to the first capacitor electrode 121 of the first layer 501. The first signal line 161 is further connectable to a processing unit to be provided at a connector end 300 of the flexible printed circuit board. An electric connection between the first capacitor electrode 121 and the first signal line 161 may be guided through the first opening 181 of the shielding component 18. The electrical connection between the first capacitor electrode 121 and the first signal line 161 may, hence, be oriented perpendicular to a plane in which the respective layers are provided. The second signal line 162 is electrically connected to the second capacitor electrode 122 of the first layer 501. The second signal line 162 is further connectable to a processing unit to be provided at a connector end 300 of the flexible printed circuit board. An electric connection between the second capacitor electrode 122 and the second signal line 162 may be guided through the second opening 182 of the shielding component 18. The electrical connection between the second capacitor electrode 122 and the second signal line 162 may, hence, be oriented perpendicular to a plane in which the respective layers are provided. The third signal line 163 is electrically connected to the third capacitor electrode 143 of the first layer 501. The third signal line 163 is further connectable to a processing unit to be provided at a connector end 300 of the flexible printed circuit board. An electric connection between the third capacitor electrode 123 and the third signal line 163 may be guided through the third opening 183 of the shielding component 18. The electrical connection between the third capacitor electrode 123 and the third signal line 163 may, hence, be oriented perpendicular to a plane in which the respective layers are provided. The fourth signal line 164 is electrically connected to the fourth capacitor electrode 124 of the first layer 501. The fourth signal line 164 is further connectable to a processing unit to be provided at a connector end 300 of the flexible printed circuit board. An electric connection between the fourth capacitor electrode 124 and the fourth signal line 164 may be guided through the fourth opening 184 of the shielding component 18. The electrical connection between the fourth capacitor electrode 124 and the fourth signal line 164 may, hence, be oriented perpendicular to a plane in which the respective layers are provided. In order to form deformation susceptibility zones, also the third layer 503 comprises the first cut-out 481, the second cut-out 482, and the third cut-out 483 of the flexible printed circuit board.

Figure 6:
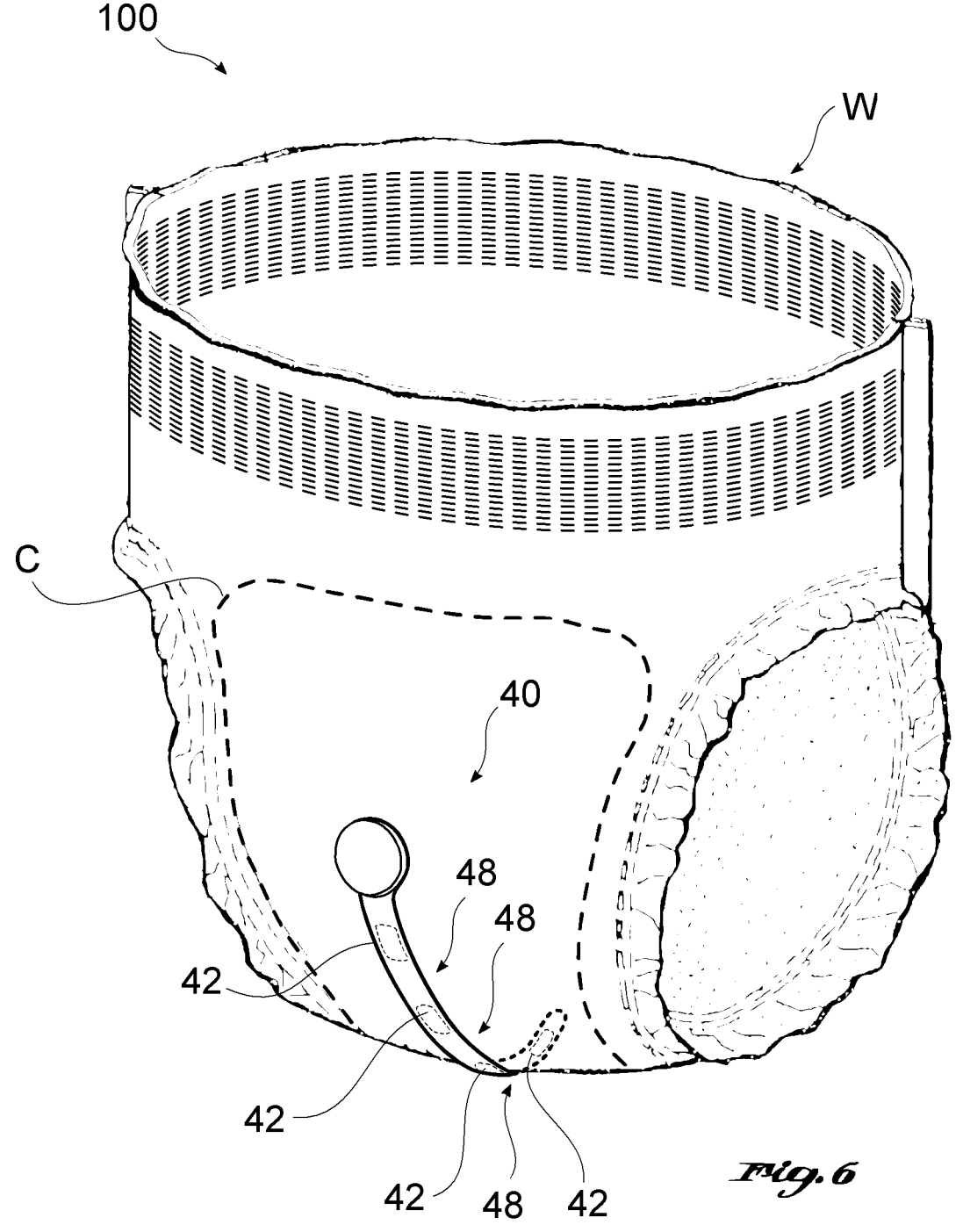
FIG. 6 is a perspective view of an embodiment of a hygiene system in accordance with the present disclosure.

FIG. 6 is a perspective view of an embodiment of a hygiene system in accordance with the present disclosure. The hygiene system in accordance with the depicted embodiment comprises: a diaper 100 having a waist region W and a crotch region C; and a strip element 40. The strip element 40 may, e.g., be the strip element of FIG. 4. The strip element 40 comprises a plurality of sensing elements 42 provided in close contact sensing zones and a plurality of deformation susceptibility zones 48. The strip element 40 is attached to a garment facing surface of the diaper 100 in a portion of the diaper 100 corresponding to crotch region C. In the depicted embodiment, attachment means such as hook fasteners are provided in the close contact sensing zones of the strip element 40. No attachment means is, however provided in the deformation susceptibility zones 48 of the strip element 40. The deformation susceptibility zones of the strip element 40 may, hence, also be flex zones in accordance with the present disclosure.

Figure 7:
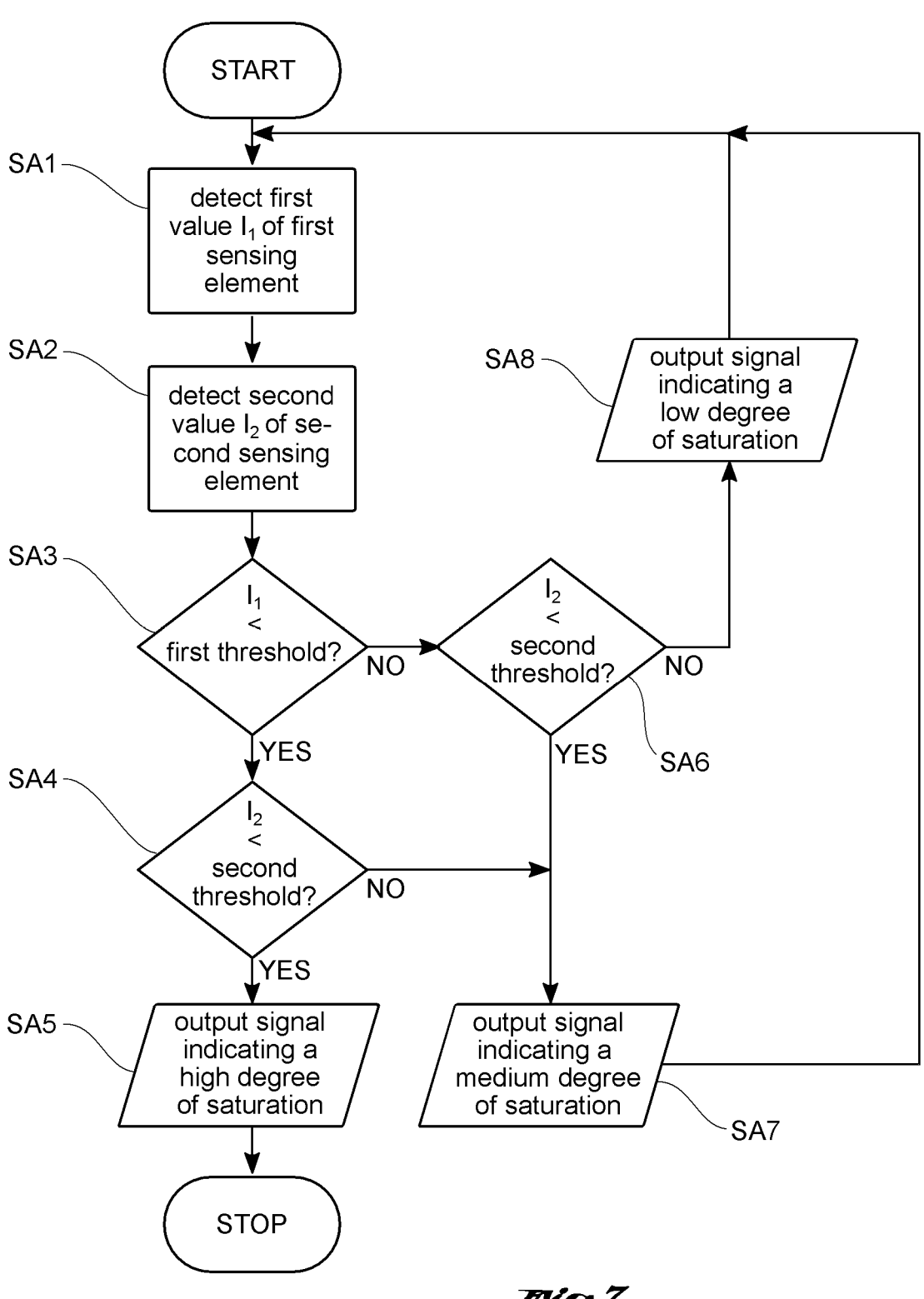
FIG. 7 is a flow diagram for illustrating an embodiment of a method in accordance with the present disclosure.

FIG. 7 is a flow diagram for illustrating an embodiment of a method in accordance with the present disclosure. The method, steps of which are depicted in FIG. 7, is a method of assessing a degree of saturation of an absorbent hygiene article, such as a diaper. The Absorbent hygiene article is internally or externally, fixedly or removably provided with a strip element, such as the strip element depicted in FIG. 3 or 4. A first step SA1 comprises a detection of a first value $I_1$ from a first sensing element of the strip element. A second step SA2 of the method comprises a detection of a second value $I_2$ from a second sensing element of the strip element. The first step SA1 and the second step SA2 may be conducted subsequently, as depicted in FIG. 7, but may also be conducted simultaneously. A third step SA3, is a step of verifying whether the first value $I_1$ is below (i.e., has fallen below) a first threshold. If the first value $I_1$ is below the first threshold, the method continues with step SA4, which is a step of verifying whether the second value $I_2$ is below (i.e., has fallen below) a second threshold. The first threshold and the second threshold may be the same thresholds. If, in step SA4, the second value $I_2$ is below the second threshold, the method continues with step SA5. Step SA5 is a step of outputting a signal indicating a high degree of saturation in the absorbent hygiene article. If, in step SA3, the second value $I_1$ is not below the first threshold, the method continues with step SA6. In step SA6, it is verified whether the second value $I_2$ is below the second threshold. In step SA6, if the second value $I_2$ is below the second threshold, the method continues with step SA7. Step SA7 is a step of outputting a signal indicating a medium degree of saturation in the absorbent hygiene article. After step SA7, the method may restart from step SA1. In step SA6, if the second value $I_2$ is not below the second threshold, the method continues with step SA8. Step SA7 is a step of outputting a signal indicating a low degree of saturation in the absorbent hygiene article. After step SA8, the method may restart from step SA1. If, in step SA4, the second value $I_2$ is not below the second threshold, the method continues with step SA7.

Figure 8:
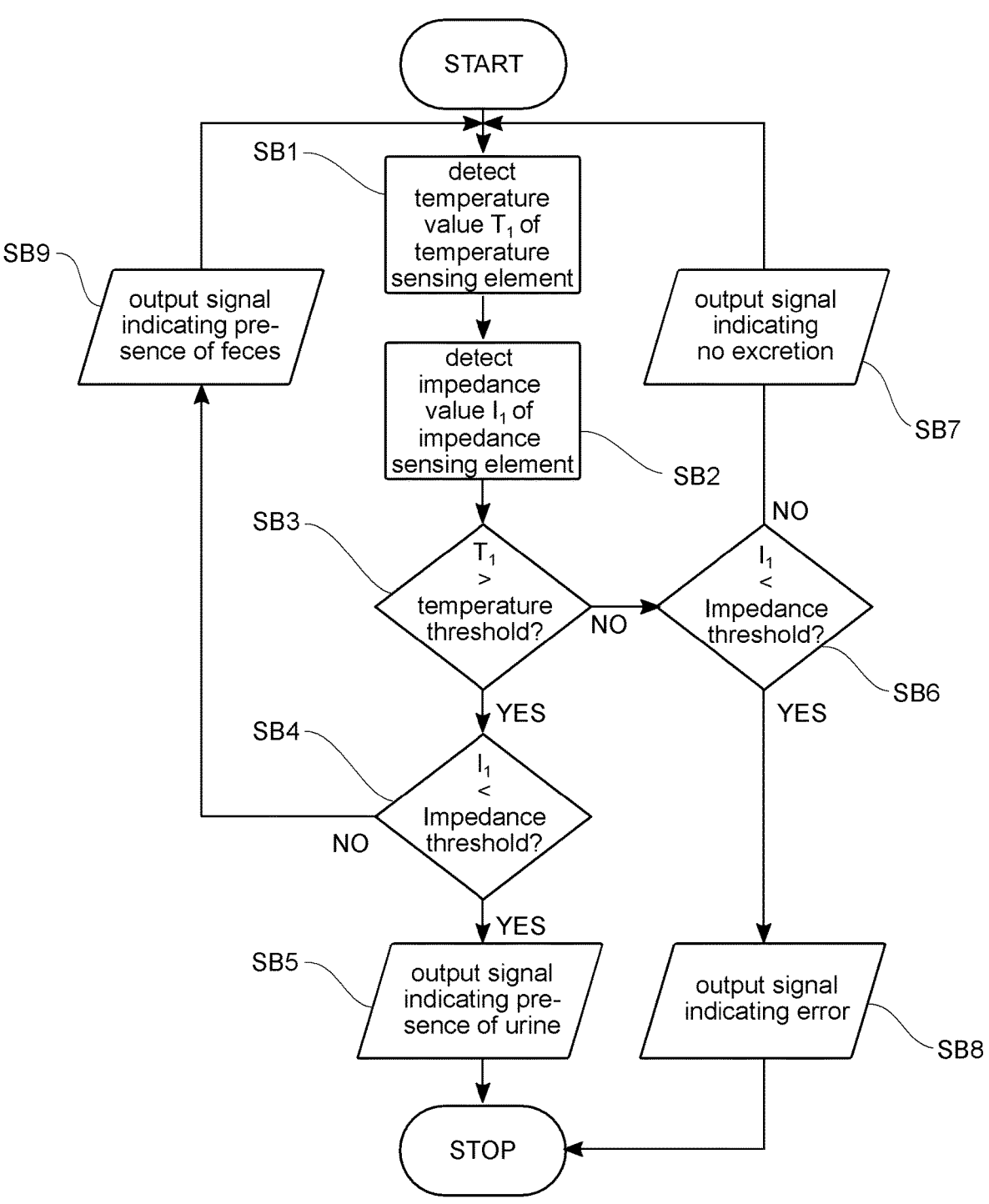
FIG. 8 is a flow diagram for illustrating an embodiment of a method in accordance with the present disclosure.

FIG. 8 is a flow diagram for illustrating an embodiment of a method in accordance with the present disclosure. The method, steps of which are depicted in FIG. 8, is a method of distinguishing between no excretion, a first type of excretion, and a second type of excretion in an absorbent hygiene article, such as a diaper, that is internally or externally, fixedly or removably provided with a strip element, such as the strip element depicted in any one of FIG. 3 or 5. The strip element utilized in the method comprises a first temperature sensing element for detecting a temperature, and a first impedance sensing element for detecting an impedance. In a first step SB1, a temperature value $T_1$ of the temperature sensing element is detected. In step SB2, an impedance value $I_1$ of the first impedance sensing element, is detected. The first step SB1 and the second step SB2 may be conducted subsequently, as depicted in FIG. 8, but may also be conducted simultaneously. After step SB2, the method continues at step SB3. In step SB3, it is determined whether the temperature value $T_1$ exceeds (i.e., has stepped over from below) a predetermined temperature threshold. If it has been determined in step SB3 that the temperature value $T_1$ exceeds the temperature threshold, the method continues at step SB4. In step SB4, it is determined whether the impedance value $I_1$ has fallen below (i.e., has stepped over from above) an impedance threshold. If it has been determined, in step SB4, that the impedance value $I_1$ has fallen below the impedance threshold, the method continues at step SB5. In step SB5, a signal indicating the presence of urine is being output. If, however, it has been determined, in step SB4, that the impedance value $I_1$ has not fallen below the impedance threshold, the method continues at step SB9. In step SB9, a signal indicating a presence of feces is being output. After step SB9, the method may restart from step SB1. If it has been determined in step SB3 that the temperature value $T_1$ does not exceeds the temperature threshold, the method continues at step SB6. In step SB6, it is determined whether the impedance value $I_1$ has fallen below the impedance threshold. If it has been determined, in step SB6, that the impedance value $I_1$ has fallen below the impedance threshold, the method continues at step SB8. In step SB8, a signal indicating an error is being output. If, however, it has been determined, in step SB6, that the impedance value $I_1$ has not fallen below the impedance threshold, the method continues at step SB7. In step SB7, a signal indicating no excretion is being output. After step SB7, the method may restart from step SB1.

While various example embodiments of devices, methods and/or uses in accordance with the present disclosure have been described above, it should be understood that they have been presented by way of example, and not limitation. It will be apparent to persons skilled in the relevant art(s) that various changes in form and detail can be made therein. Thus, the present disclosure should not be limited by any of the above described example embodiments but should be defined only in accordance with the following claims and their equivalents.

Further, it is to be understood that certain features described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

The invention claimed is:

1. A strip element configured to be internally or externally, fixedly or removably provided to an absorbent hygiene article, the strip element comprising at least a first sensing element for measuring an impedance, the first sensing element having a capacitor electrode, a signal line, and a ground element, wherein the capacitor electrode is electrically connected to the signal line, wherein the first sensing element further comprises a shielding component provided between the signal line and the ground element, and wherein the strip element is configured such that an electric potential of the shielding component synchronously oscillates with an electric potential of the signal line.

2. The strip element of claim 1, further comprising a second sensing element for measuring an impedance, the second sensing element having a second capacitor electrode, a second signal line, and a second ground element, wherein the second capacitor electrode is electrically connected to the second signal line, wherein the second sensing element further comprises a second shielding component provided between the second signal line and the second ground element, and wherein the strip element is configured such that an electric potential of the second shielding component synchronously oscillates with an electric potential of the second signal line.

3. The strip element of claim 2, wherein the first shielding component and the second shielding component are electrically connected to each other.

4. The strip element of claim 1, wherein the ground element comprises a ground electrode and a ground line electrically connected thereto, and wherein the shielding component is provided between the signal line and the ground electrode, and also between the signal line and the ground line.

5. The strip element of claim 1, wherein the shielding component is, at least partially, provided between the capacitor electrode and the signal line.

6. The strip element of claim 1, wherein the shielding component comprises an opening in which a portion of the signal line is provided so as to be guided from a first side of the shielding component to a second side of the shielding component, the first side being a side in which the capacitor electrode is provided.

7. The strip element of claim 1, further comprising a plurality of layers including first to third layers stacked in numerical order, the first layer including at least one of, optionally both of the ground electrode and the capacitor electrode, the second layer including the shielding component, and the third layer including at least parts of the signal line, the first to third layers optionally being substantially parallel.

8. The strip element of claim 7, wherein an insulating layer is provided between the first layer and the second layer, and between the second layer and the third layer.

9. The strip element of claim 7, wherein the first to third layers are layers of a flexible printed circuit board.

10. The strip element of claim 9, wherein the flexible printed circuit board comprises at least one of: polyimide; polyester; polytetrafluoroethylene; aramid; and polyethylene naphthalate.

11. The strip element of claim 9, wherein the flexible printed circuit board comprises the first sensing element and the second sensing element.

12. The strip element of claim 1, wherein the shielding component is continuously provided between the ground element and the signal line such that there is no portion of the sensing element in which the shielding component is not provided between the ground element and the signal line, the ground element optionally including a ground electrode and a ground line.

13. The strip element of claim 1, wherein the ground element comprises a ground electrode and a ground line electrically connected thereto, wherein the shielding component is continuously provided between the ground electrode and the signal line such that there is no portion of the sensing element in which the shielding component is not provided between the ground electrode and the signal line, and wherein the shielding component is optionally not provided between the ground line and the signal line.

14. A use of the strip element of claim 1, wherein the sensing element is attached to a garment facing surface of an absorbent hygiene article, and wherein the first layer is provided closer to the garment facing surface than the second layer and/or the third layer.

15. A strip element configured to be internally or externally, fixedly or removably provided to an absorbent hygiene article, the strip element comprising a sensing element for measuring an impedance, the sensing element having a capacitor electrode, a signal line, and a ground element, wherein the capacitor electrode is electrically connected to the signal line, wherein the first sensing element further comprises a shielding component provided between the signal line and the ground element, and wherein the strip element is configured such that an electric potential of the shielding component synchronously oscillates with an electric potential of the signal line wherein one of the capacitor electrode and the ground element is provided so as to form an open or a closed loop around the other one of the capacitor electrode and the ground element.

16. The strip element of claim 15, wherein a ground electrode of the ground element is formed so as to form an open or closed loop around the capacitor electrode.

17. The strip element of claim 15 wherein a ground electrode of the ground element is provided in a first layer of a flexible printed circuit board, wherein the capacitor electrode is provided in a layer of the flexible printed circuit board, and wherein the first layer comprising the ground electrode and the layer comprising the capacitor electrode are optionally the same layers.

18. A hygiene system comprising an absorbent hygiene article, and the strip element of claim 1, the strip element being attached or removably attachable to a garment facing surface of the absorbent hygiene article, wherein the hygiene system is configured such that no galvanic contact is establishable between any one of the at least two sensing elements and a liquid to be absorbed by the absorbent hygiene article.

19. The hygiene system of claim 18, wherein the absorbent hygiene article comprises a first indication means for indicating, to a user, a first designated location for attaching the strip element to a garment facing surface the absorbent hygiene article.

20. The hygiene system of claim 19, wherein the absorbent hygiene article further comprises a second indication means for indicating, to a user, a second designated location for attaching the strip element to a garment facing surface of the absorbent hygiene article.

* * * * *